United States Patent
Witztum et al.

(10) Patent No.: US 11,008,381 B2
(45) Date of Patent: May 18, 2021

(54) ANTIBODIES TO OXIDIZED PHOSPHOLIPIDS

(71) Applicant: The Regents of the University of California, Oakland, CA (US)

(72) Inventors: Joseph L. Witztum, San Diego, CA (US); Sotirios Tsimikas, San Diego, CA (US); Xuchu Que, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 246 days.

(21) Appl. No.: 15/991,662

(22) Filed: May 29, 2018

(65) Prior Publication Data

US 2018/0334497 A1 Nov. 22, 2018

Related U.S. Application Data

(63) Continuation of application No. 14/770,160, filed as application No. PCT/US2014/018402 on Feb. 25, 2014, now abandoned.

(60) Provisional application No. 61/769,154, filed on Feb. 25, 2013, provisional application No. 61/894,220, filed on Oct. 22, 2013.

(51) Int. Cl.
*C07K 16/18* (2006.01)
*A01K 67/027* (2006.01)
*A61K 39/00* (2006.01)

(52) U.S. Cl.
CPC .......... *C07K 16/18* (2013.01); *A01K 67/0275* (2013.01); *A01K 67/0278* (2013.01); *A01K 2217/052* (2013.01); *A01K 2217/15* (2013.01); *A01K 2217/206* (2013.01); *A01K 2227/105* (2013.01); *A01K 2267/01* (2013.01); *A01K 2267/0362* (2013.01); *A01K 2267/0368* (2013.01); *A01K 2267/0375* (2013.01); *A61K 2039/505* (2013.01); *C07K 2317/24* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| 7,939,287 B2* | 5/2011 | Tsimikas | C12Q 1/6883 435/11 |
| 2009/0130776 A1 | 5/2009 | Imamura et al. | |
| 2012/0149596 A1 | 6/2012 | Tsimikas et al. | |
| 2014/0193413 A1* | 7/2014 | Pettersson | A61P 9/10 424/135.1 |

FOREIGN PATENT DOCUMENTS

WO 2011/038786 A 4/2011

OTHER PUBLICATIONS

Bai, Lingfei, "International Preliminary Report on Patentability and Written Opinion," PCT/US2014/018402, The International Bureau of WIPO, dated Sep. 3, 2015.
Casset et al., "A peptide mimetic of an anti-CD4 monoclonal antibody by rational design," Biochem. Biophys. Res. Commun., 307:198-205, 2003.
Chen et al., "Selection and Analysis of an Optimized Anti-VEGF Antibody: Crystal Structure of an Affinity-matured Fab in Complex with Antigen," J. Mol. Biol., 293:865-881, 1999.
Lamminmaki et al., "Crystal Structure of a Recombinant Anti-estradiol Fab Fragment in Complex with 17(beta)-Estradiol," J. of Biol. Chem., 276(39):36687-36694, 2001.
MacCallum et al., "Antibody-antigen Interactions: Contact Analysis and Binding Site Topography," J. Mol. Biol., 262:732-745, 1996.
Padlan et al., "Structure of an antibody-antigen complex: Crystal Structure fo the HyHEL-10 Fab-lysozyme complex," Proc. Natl. Acad. Sci. USA, 86:5938-5942, 1989.
De Passcalis et al., "Grafting of 'Abbreviated' Complexmentarity-Determining Regions Containing Specificity-Determining Residues Essential for Ligan Contact to Engineer a Less Immunogenic Humanized Monoclonal Antibody," J. of Immunol., 169:3076-3084, 2002.
Rudikoff et al., "Single amino acid substitution altering antigen-binding specificity," Proc. Natl. Acad. Sci. USA, 79:1979-1983, 1982.
Vajdos et al., "Comprehensive Functional Maps fo the Antigen-binding Site of an Anti-ErbB2 Antibody Obtained with Shotgun Scanning Mutagenesis," J. Mol. Biol., 320:415-428, 2002.
Wu et al., "Humanization of a Murine Monoclonal Antibody by Simultaneous Optimization of Framework and CDR Residues," J. Mol. Biol., 294:151-162, 1999.
Thomas, Shane, "International Search Report and Written Opinion," PCT/US2014/018402, United States Patent & Trademark Office, dated Aug. 11, 2014.

\* cited by examiner

*Primary Examiner* — Sharon X Wen
(74) *Attorney, Agent, or Firm* — Gavrilovich, Dodd & Lindsey LLP

(57) ABSTRACT

The disclosure provides for single chain variable fragments to oxidized phospholipid epitopes and methods of use thereof, including the production of transgenic animal models and the use of the fragments as therapeutic agents for treating CAS.

15 Claims, 20 Drawing Sheets
Specification includes a Sequence Listing.

Plasma SAA Levels Increase in Response to
High-Fat Diets in LDLR$^{-/-}$ Mice

|  | Chow (n=5), μg/mL | HF (n=10), μg/mL | HF and Cholesterol (n=10), μg/mL | P* |
| --- | --- | --- | --- | --- |
| 5 weeks | 8.4±1.2 | 34.8±5.2 | 55.9±8.2 | 0.005 |
| 10 weeks | 5.7±1.1 | 28.5±7.7 | 61.5±16.0 | <0.05 |

Values shown are mean±SEM. The number of mice is shown in parentheses.
HF indicates high fat.

E06scFv-Ig
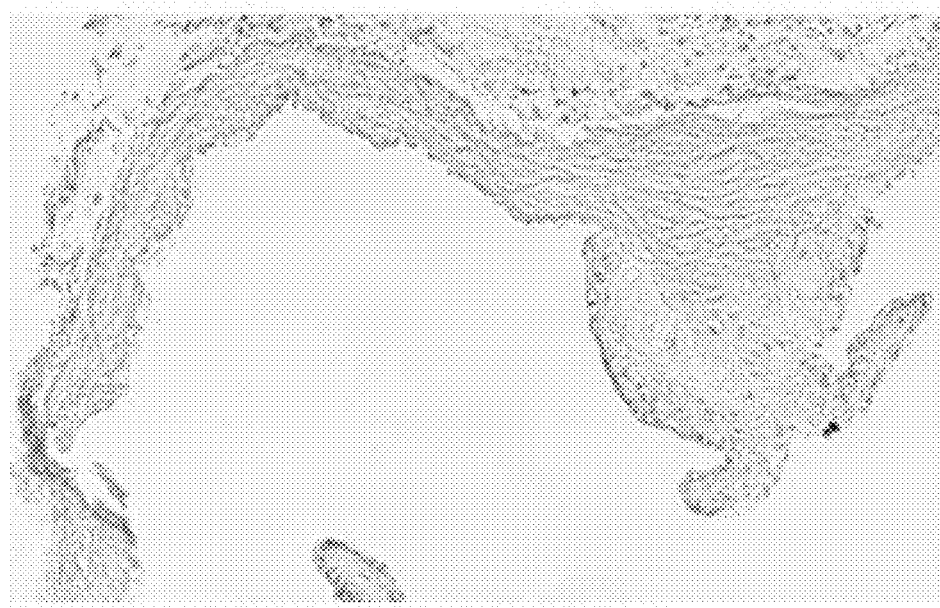
LDLR-/- Ctrl
FIGURE 16

>E06scFv antibody fragment
(From 1 to 930. Translation 309 a.a. MW=33.65 kDa)

```
  1 ATGGAGACAGACACACTCCTGCTATGGGTACTGCTGCTCTGGGTTCCAGGTTCCACTGGTGACGCGGCCCAGCCG
  1  M  E  T  D  T  L  L  L  W  V  L  L  L  W  V  P  G  S  T  G  D  A  A  Q  P

76 GCCAGGCGCGCCGTACGAAGCTTAGACATTGTGATGACTCAGTCTCCATCTTCCCTTTCTGTGTCAGCAGGTAAG
 26  A  R  R  A  V  R  S  L  D  I  V  M  T  Q  S  P  S  S  L  S  V  S  A  G  K

151 AAGGTCACCATTAGTTGCACGGCCAGTGAGAGCCTTTATTCAAGCAAACACAAGGTGCACTACTTGGCTTGGTAC
 51  K  V  T  I  S  C  T  A  S  E  S  L  Y  S  S  K  H  K  V  H  Y  L  A  W  Y

226 CAGAAGAAACCAGAGCAATCTCCTAAACTGCTGATATACGGGGCATCCAACCGATACATTGGGGTCCCTGATCGC
 76  Q  K  K  P  E  Q  S  P  K  L  L  I  Y  G  A  S  N  R  Y  I  G  V  P  D  R

301 TTCACAGGCAGTGGATCTGGGACAGATTTCACTCTGACCATCAGCAGTGTACAGGTTGAAGACCTCACACATTAT
101  F  T  G  S  G  S  G  T  D  F  T  L  T  I  S  S  V  Q  V  E  D  L  T  H  Y

376 TACTGTGCACAGTTTTACAGCTATCCGCTCACGTTCGGTGCTGGGACCAAGCTGGAAATCAAAGGTGGTGGAGGA
126  Y  C  A  Q  F  Y  S  Y  P  L  T  F  G  A  G  T  K  L  E  I  K  G  G  G

451 TCAGGTGGAGGTGGTTCAGGAGGTGGCGGATCCGAGGTGAAGCTGGTGGAGTCTGGAGGAGGCTTGGTACAGCCT
151  S  G  G  G  S  G  G  G  G  S  E  V  K  L  V  E  S  G  G  G  L  V  Q  P

526 GGGGGTTCTCTGAGACTCTCCTGTGCAACTTCTGGGTTCACCTTCAGTGATTTCTACATGGAGTGGGTCCGCCAG
176  G  G  S  L  R  L  S  C  A  T  S  G  F  T  F  S  D  F  Y  M  E  W  V  R  Q

601 GCTCCAGGGAAGAGACTGGAGTGGATTGCTGCAAGTAGAAACAAAGCTAATGATTATACAACAGAGTACGCTGAC
201  A  P  G  K  R  L  E  W  I  A  A  S  R  N  K  A  N  D  Y  T  T  E  Y  A  D

676 TCTGTGAAGGGTCGGTTCATCGTCTCCAGAGACACTTCCCAAAGCATCCTCTACCTTCAGATGAATGCCCTGAGA
226  S  V  K  G  R  F  I  V  S  R  D  T  S  Q  S  I  L  Y  L  Q  M  N  A  L  R

751 GCCGAGGACACTGCCATTTATTACTGTGCAAGAGATTACTACGGTAGTAGCTACTGGTACTTCGATGTCTGGGGC
251  A  E  D  T  A  I  Y  Y  C  A  R  D  Y  Y  G  S  S  Y  W  Y  F  D  V  W  G

826 GCAGGGACCACGGTCACCGTCTCCTCTCGAGGAGGGCCCGAACAAAAACTCATCTCAGAAGAGGATCTGAATAGC
276  A  G  T  T  V  T  V  S  S  R  G  G  P  E  Q  K  L  I  S  E  E  D  L  N  S

901 GCCGTCGACCATCATCATCATCATCATTGA
301  A  V  D  H  H  H  H  H  H  *
```

Annotation:
A.A. 1 ... 33 = Ig kappa chain leader sequence for antibody secretion.
A.A. 34 ... 146 = E06 light-chain variable region.
A.A. 42 ... 49 = FW1 region TFLAVTAS mutated to SSLSVSAG to enhance affinity to OxPL-PC/OxLDL and functional activity.
A.A. 57 ... 73 = "TASESLYSSKHKVHYLA" E06 L-chain CDR1.
A.A. 89 ... 95 = "GASNRYI" E06 L-chain CDR2.
A.A. 127 ... 136 = "CAQFYSYPLT" E06 L-chain CDR3.
A.A. 147 ... 161 = (Gly4Ser)x3 flexible linker peptides.
A.A. 162 ... 284 = E06 heavy-chain variable region with triple mutations of P201A, S224A and A225D to       increase antibody affinity to OxPL-PC/OxLDL.
A.A. 187 ... 193 = "GFTFSDF" E06 H-chain CDR1.
A.A. 213 ... 220 = "RNKANDYT" E06 H-chain CDR2.
A.A. 259 ... 274 = "CARDYYGSSYWYFDVW" E06 H-chain CDR3.
A.A. 289 ... 298 = myc epitope tag
A.A. 304 ... 309 = polyHis tag.

FIGURE 20

```
>Chimeric E06scFv-human IgG1-Fc antibody sequence
(DNA sequence From 1 to 1587. Translation 528 a.a. MW=58kDa)

1 ATGGAGACAGACACACTCCTGCTATGGGTACTGCTGCTCTGGGTTCCAGGTTCCACTGGTGACGCGGCCCAGCCG
   1 M  E  T  D  T  L  L  L  W  V  L  L  L  W  V  P  G  S  T  G  D  A  A  Q  P

76 GCCAGGCGCGCCGTACGAAGCTTAGACATTGTGATGACTCAGTCTCCATCTTCCCTTTCTGTGTCAGCAGGTAAG
  26 A  R  R  A  V  R  S  L  D  I  V  M  T  Q  S  P  S  S  L  S  V  S  A  G  K

151 AAGGTCACCATTAGTTGCACGGCCAGTGAGAGCCTTTATTCAAGCAAACACAAGGTGCACTACTTGGCTTGGTAC
  51 K  V  T  I  S  C  T  A  S  E  S  L  Y  S  S  K  H  K  V  H  Y  L  A  W  Y

226 CAGAAGAAACCAGAGCAATCTCCTAAACTGCTGATATACGGGGCATCCAACCGATACATTGGGGTCCCTGATCGC
  76 Q  K  K  P  E  Q  S  P  K  L  L  I  Y  G  A  S  N  R  Y  I  G  V  P  D  R

301 TTCACAGGCAGTGGATCTGGGACAGATTTCACTCTGACCATCAGCAGTGTACAGGTTGAAGACCTCACACATTAT
 101 F  T  G  S  G  S  G  T  D  F  T  L  T  I  S  S  V  Q  V  E  D  L  T  H  Y

376 TACTGTGCACAGTTTTACAGCTATCCGCTCACGTTCGGTGCTGGGACCAAGCTGGAAATCAAAGGTGGTGGAGGA
 126 Y  C  A  Q  F  Y  S  Y  P  L  T  F  G  A  G  T  K  L  E  I  K  G  G  G  G

451 TCAGGTGGAGGTGGTTCAGGAGGTGGCGGATCCGAGGTGAAGCTGGTGGAGTCTGGAGGAGGCTTGGTACAGCCT
 151 S  G  G  G  G  S  G  G  G  G  S  E  V  K  L  V  E  S  G  G  G  L  V  Q  P

526 GGGGGTTCTCTGAGACTCTCCTGTGCAACTTCTGGGTTCACCTTCAGTGATTTCTACATGGAGTGGGTCCGCCAG
 176 G  G  S  L  R  L  S  C  A  T  S  G  F  T  F  S  D  F  Y  M  E  W  V  R  Q

601 GCTCCAGGGAAGAGACTGGAGTGGATTGCTGCAAGTAGAAACAAAGCTAATGATTATACAACAGAGTACGCTGAC
 201 A  P  G  K  R  L  E  W  I  A  A  S  R  N  K  A  N  D  Y  T  T  E  Y  A  D

676 TCTGTGAAGGGTCGGTTCATCGTCTCCAGAGACACTTCCCAAAGCATCCTCTACCTTCAGATGAATGCCCTGAGA
 226 S  V  K  G  R  F  I  V  S  R  D  T  S  Q  S  I  L  Y  L  Q  M  N  A  L  R

751 GCCGAGGACACTGCCATTTATTACTGTGCAAGAGATTACTACGGTAGTAGCTACTGGTACTTCGATGTCTGGGGC
 251 A  E  D  T  A  I  Y  Y  C  A  R  D  Y  Y  G  S  S  Y  W  Y  F  D  V  W  G

826 GCAGGGACCACGGTCACCGTCTCCTCTCTGGACCCGAAGTCTTCTGACAAAACTtACACATGCCCACCGTGCCCA
 276 A  G  T  T  V  T  V  S  S  L  D  P  K  S  S  D  K  T  Y  T  C  P  P  C  P

901 GCACCTGAACTCCTGGGGGGACCGTCAGTCTTCCTCTTCCCCCCAAAACCCAAGGACACCCTCATGATCTCCCGG
 301 A  P  E  L  L  G  G  P  S  V  F  L  F  P  P  K  P  K  D  T  L  M  I  S  R

976 ACCCCTGAGGTCACATGCGTGGTGGTGGACGTGAGCCACGAAGACCCTGAGGTCAAGTTCAACTGGTACGTGGAC
 326 T  P  E  V  T  C  V  V  V  D  V  S  H  E  D  P  E  V  K  F  N  W  Y  V  D

1051 GGCGTGGAGGTGCATAATGCCAAGACAAAGCCGCGGGAGGAGCAGTACAACAGCACGTACCGTGTGGTCAGCGTC
 351 G  V  E  V  H  N  A  K  T  K  P  R  E  E  Q  Y  N  S  T  Y  R  V  V  S  V

1126 CTCACCGTCCTGCACCAGGACTGGCTGAATGGCAAGGAGTACAAGTGCAAGGTCTCCAACAAAGCCCTCCCAGCC
 376 L  T  V  L  H  Q  D  W  L  N  G  K  E  Y  K  C  K  V  S  N  K  A  L  P  A

1201 CCCATCGAGAAAACCATCTCCAAAGCCAAAGGGCAGCCCCGAGAACCACAGGTGTACACCCTGCCCCCATCCCGG
 401 P  I  E  K  T  I  S  K  A  K  G  Q  P  R  E  P  Q  V  Y  T  L  P  P  S  R

1276 GAGGAGATGACCAAGAACCAGGTCAGCCTGACCTGCCTGGTCAAAGGCTTCTATCCCAGCGACATCGCCGTGGAG
 426 E  E  M  T  K  N  Q  V  S  L  T  C  L  V  K  G  F  Y  P  S  D  I  A  V  E

1351 TGGGAGAGCAATGGGCAGCCGGAGAACAACTACAAGACCACGCCTCCCGTGCTGGACTCCGACGGCTCCTTCTTC
 451 W  E  S  N  G  Q  P  E  N  N  Y  K  T  T  P  P  V  L  D  S  D  G  S  F  F
```

FIGURE 21

```
1426 CTCTACAGCAAGCTCACCGTGGACAAGAGCAGGTGGCAGCAGGGGAACGTCTTCTCATGCTCCGTGATGCACGAG
 476  L   Y   S   K   L   T   V   D   K   S   R   W   Q   Q   G   N   V   F   S   C   S   V   M   H   E

1501 GCTCTGCACAACCACTACACGCAGAAGAGCCTCTCCCTGTCTCCGGGTAAAGGtGGaGGtGGATCACATCATCAT
 501  A   L   H   N   H   Y   T   Q   K   S   L   S   L   S   P   G   K   G   G   G   G   S   H   H   H

1576 CATCATCATTAA
 526  H   H   H   *
```

Annotation:
A.A. 1 … 33 = Ig kappa chain leader sequence for antibody secretion.
A.A. 34 … 146 = E06 light-chain variable region.
A.A. 42 … 49 = FW1 region TFLAVTAS mutated to SSLSVSAG to enhance affinity to OxPL-PC/OxLDL and functional activity.
A.A. 57 … 73 = "TASESLYSSKHKVHYLA" E06 L-chain CDR1.
A.A. 89 … 95 = "GASNRYI" E06 L-chain CDR2.
A.A. 127 … 136 = "CAQFYSYPLT" E06 L-chain CDR3.
A.A. 147 … 161 = (Gly4Ser)x3 flexible linker peptides.
A.A. 162 … 284 = E06 heavy-chain variable region with triple mutations of P201A, S224A and A225D to increase antibody affinity to OxPL-PC/OxLDL.
A.A. 187 … 193 = "GFTFSDF" E06 H-chain CDR1.
A.A. 213 … 220 = "RNKANDYT" E06 H-chain CDR2.
A.A. 259 … 274 = "CARDYYGSSYWYFDVW" E06 H-chain CDR3.
A.A. 285 … 517 = human IgG1-Fc region with Hinge-(LDPKSSDKTYTCPPCP)-modification of C290S and H294Y to increase ADCC activity.
A.A. 518 … 528 = Gly4Ser peptides linked with 6xHis-tag.

SEQUENCE LISTING

```
<160> NUMBER OF SEQ ID NOS: 14

<210> SEQ ID NO 1
<211> LENGTH: 930
<212> TYPE: DNA
<213> ORGANISM: Artificial Sequence
<220> FEATURE:
<223> OTHER INFORMATION: Engineered scFV E06 Antibody domain
<220> FEATURE:
<221> NAME/KEY: CDS
<222> LOCATION: (1)..(930)

<400> SEQUENCE: 1 atg gag aca gac aca ctc ctg cta tgg gta ctg ctg ctc tgg gtt cca        48
Met Glu Thr Asp Thr Leu Leu Leu Trp Val Leu Leu Leu Trp Val Pro
1               5                   10                  15 ggt tcc act ggt gac gcg gcc cag ccg gcc agg cgc gcc gta cga agc        96
Gly Ser Thr Gly Asp Ala Ala Gln Pro Ala Arg Arg Ala Val Arg Ser
            20                  25                  30 tta gac att gtg atg act cag tct cca tct tcc ctt tct gtg tca gca       144
Leu Asp Ile Val Met Thr Gln Ser Pro Ser Ser Leu Ser Val Ser Ala
        35                  40                  45 ggt aag aag gtc acc att agt tgc acg gcc agt gag agc ctt tat tca       192
Gly Lys Lys Val Thr Ile Ser Cys Thr Ala Ser Glu Ser Leu Tyr Ser
    50                  55                  60 agc aaa cac aag gtg cac tac ttg gct tgg tac cag aag aaa cca gag       240
Ser Lys His Lys Val His Tyr Leu Ala Trp Tyr Gln Lys Lys Pro Glu
65                  70                  75                  80 caa tct cct aaa ctg ctg ata tac ggg gca tcc aac cga tac att ggg       288
Gln Ser Pro Lys Leu Leu Ile Tyr Gly Ala Ser Asn Arg Tyr Ile Gly
                85                  90                  95 gtc cct gat cgc ttc aca ggc agt gga tct ggg aca gat ttc act ctg       336
Val Pro Asp Arg Phe Thr Gly Ser Gly Ser Gly Thr Asp Phe Thr Leu
            100                 105                 110 acc atc agc agt gta cag gtt gaa gac ctc aca cat tat tac tgt gca       384
Thr Ile Ser Ser Val Gln Val Glu Asp Leu Thr His Tyr Tyr Cys Ala
        115                 120                 125 cag ttt tac agc tat ccg ctc acg ttc ggt gct ggg acc aag ctg gaa       432
Gln Phe Tyr Ser Tyr Pro Leu Thr Phe Gly Ala Gly Thr Lys Leu Glu
    130                 135                 140 atc aaa ggt ggt gga gga tca ggt gga ggt ggt tca gga ggt ggc gga       480
Ile Lys Gly Gly Gly Gly Ser Gly Gly Gly Gly Ser Gly Gly Gly Gly
145                 150                 155                 160 tcc gag gtg aag ctg gtg gag tct gga gga ggc ttg gta cag cct ggg       528
Ser Glu Val Lys Leu Val Glu Ser Gly Gly Gly Leu Val Gln Pro Gly
                165                 170                 175 ggt tct ctg aga ctc tcc tgt gca act tct ggg ttc acc ttc agt gat       576
Gly Ser Leu Arg Leu Ser Cys Ala Thr Ser Gly Phe Thr Phe Ser Asp
            180                 185                 190 ttc tac atg gag tgg gtc cgc cag gct cca ggg aag aga ctg gag tgg       624
Phe Tyr Met Glu Trp Val Arg Gln Ala Pro Gly Lys Arg Leu Glu Trp
        195                 200                 205
```

```
att gct gca agt aga aac aaa gct aat gat tat aca aca gag tac gct    672
Ile Ala Ala Ser Arg Asn Lys Ala Asn Asp Tyr Thr Thr Glu Tyr Ala
    210                 215                 220 gac tct gtg aag ggt cgg ttc atc gtc tcc aga gac act tcc caa agc    720
Asp Ser Val Lys Gly Arg Phe Ile Val Ser Arg Asp Thr Ser Gln Ser
225                 230                 235                 240 atc ctc tac ctt cag atg aat gcc ctg aga gcc gag gac act gcc att    768
Ile Leu Tyr Leu Gln Met Asn Ala Leu Arg Ala Glu Asp Thr Ala Ile
                245                 250                 255 tat tac tgt gca aga gat tac tac ggt agt agc tac tgg tac ttc gat    816
Tyr Tyr Cys Ala Arg Asp Tyr Tyr Gly Ser Ser Tyr Trp Tyr Phe Asp
            260                 265                 270 gtc tgg ggc gca ggg acc acg gtc acc gtc tcc tct cga gga ggg ccc    864
Val Trp Gly Ala Gly Thr Thr Val Thr Val Ser Ser Arg Gly Gly Pro
        275                 280                 285 gaa caa aaa ctc atc tca gaa gag gat ctg aat agc gcc gtc gac cat    912
Glu Gln Lys Leu Ile Ser Glu Glu Asp Leu Asn Ser Ala Val Asp His
    290                 295                 300 cat cat cat cat cat tga                                            930
His His His His His
305
```

```
<210> SEQ ID NO 2
<211> LENGTH: 309
<212> TYPE: PRT
<213> ORGANISM: Artificial Sequence
<220> FEATURE:
<223> OTHER INFORMATION: Synthetic Construct

<400> SEQUENCE: 2
```

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Asp Ile Val Met Thr Gln Ser Pro Ser Ser Leu Ser Val Ser Ala
        35                  40                  45

Gly Lys Lys Val Thr Ile Ser Cys Thr Ala Ser Glu Ser Leu Tyr Ser
    50                  55                  60

Ser Lys His Lys Val His Tyr Leu Ala Trp Tyr Gln Lys Lys Pro Glu
65                  70                  75                  80

Gln Ser Pro Lys Leu Leu Ile Tyr Gly Ala Ser Asn Arg Tyr Ile Gly
                85                  90                  95

Val Pro Asp Arg Phe Thr Gly Ser Gly Ser Gly Thr Asp Phe Thr Leu
            100                 105                 110

Thr Ile Ser Ser Val Gln Val Glu Asp Leu Thr His Tyr Tyr Cys Ala
        115                 120                 125

Gln Phe Tyr Ser Tyr Pro Leu Thr Phe Gly Ala Gly Thr Lys Leu Glu
    130                 135                 140

Ile Lys Gly Gly Gly Gly Ser Gly Gly Gly Gly Ser Gly Gly Gly Gly
145                 150                 155                 160

Ser Glu Val Lys Leu Val Glu Ser Gly Gly Gly Leu Val Gln Pro Gly
                165                 170                 175

Gly Ser Leu Arg Leu Ser Cys Ala Thr Ser Gly Phe Thr Phe Ser Asp
            180                 185                 190

Phe Tyr Met Glu Trp Val Arg Gln Ala Pro Gly Lys Arg Leu Glu Trp
        195                 200                 205

Ile Ala Ala Ser Arg Asn Lys Ala Asn Asp Tyr Thr Thr Glu Tyr Ala
    210                 215                 220
```

```
Asp Ser Val Lys Gly Arg Phe Ile Val Ser Arg Asp Thr Ser Gln Ser
225                 230                 235                 240

Ile Leu Tyr Leu Gln Met Asn Ala Leu Arg Ala Glu Asp Thr Ala Ile
            245                 250                 255

Tyr Tyr Cys Ala Arg Asp Tyr Tyr Gly Ser Ser Tyr Trp Tyr Phe Asp
        260                 265                 270

Val Trp Gly Ala Gly Thr Thr Val Thr Val Ser Ser Arg Gly Gly Pro
275                 280                 285

Glu Gln Lys Leu Ile Ser Glu Glu Asp Leu Asn Ser Ala Val Asp His
    290                 295                 300

His His His His His
305
```

<210> SEQ ID NO 3
<211> LENGTH: 1554
<212> TYPE: DNA
<213> ORGANISM: Artificial Sequence
<220> FEATURE:
<223> OTHER INFORMATION: Humanized E06 single-chain antibody with
      IgG1-Fc (E06scFv-Fc)
<220> FEATURE:
<221> NAME/KEY: CDS
<222> LOCATION: (1)..(1554)

<400> SEQUENCE: 3

```
atg gag acc gac aca ctg ttg ttg tgg gtg ttg ctc tgg gtg cca         48
Met Glu Thr Asp Thr Leu Leu Leu Trp Val Leu Leu Trp Val Pro
1               5                   10                  15 gga agc aca ggt gac gct gct gac atc gtc atg acc cag agc ccc gac     96
Gly Ser Thr Gly Asp Ala Ala Asp Ile Val Met Thr Gln Ser Pro Asp
                20                  25                  30 tct ctc gcg gtt tct ctg gga gag cgg gca aca atc aac tgc aca gca    144
Ser Leu Ala Val Ser Leu Gly Glu Arg Ala Thr Ile Asn Cys Thr Ala
            35                  40                  45 agc gaa tcc ctg tac tca tcc aag cac gtg cat tac ctc gct tgg tac    192
Ser Glu Ser Leu Tyr Ser Ser Lys His Val His Tyr Leu Ala Trp Tyr
        50                  55                  60 cag cag aaa cca ggg caa cca cca aag ctc ctc att tat ggg gcc agc    240
Gln Gln Lys Pro Gly Gln Pro Pro Lys Leu Leu Ile Tyr Gly Ala Ser
65                  70                  75                  80 aac aga tat att gga gtc cca gat cga ttc agc ggt tcc ggc tcc gga    288
Asn Arg Tyr Ile Gly Val Pro Asp Arg Phe Ser Gly Ser Gly Ser Gly
                85                  90                  95 aca gac ttt acc ctc acg ata agc agc ctg cag gcg gaa gat gtg gcc    336
Thr Asp Phe Thr Leu Thr Ile Ser Ser Leu Gln Ala Glu Asp Val Ala
            100                 105                 110 gtg tat tac tgc gca caa ttc tac agc tat cct ctg acc ttc gga gga    384
Val Tyr Tyr Cys Ala Gln Phe Tyr Ser Tyr Pro Leu Thr Phe Gly Gly
        115                 120                 125 gga aca aaa gtg gag atc aaa ggc gga ggt gga tcc gga ggg ggt gga    432
Gly Thr Lys Val Glu Ile Lys Gly Gly Gly Gly Ser Gly Gly Gly Gly
130                 135                 140 tct gga ggt ggc ggt agt gaa gtg cag ctg gtg gaa agt gga ggc ggc    480
Ser Gly Gly Gly Gly Ser Glu Val Gln Leu Val Glu Ser Gly Gly Gly
145                 150                 155                 160 ctg gtg caa cca ggt ggc tct ctg agg ctg tca tgc gct gcc tct gga    528
Leu Val Gln Pro Gly Gly Ser Leu Arg Leu Ser Cys Ala Ala Ser Gly
                165                 170                 175 ttt acc ttc tca gat ttc tac atg gaa tgg gtc aga caa gcc cct gga    576
Phe Thr Phe Ser Asp Phe Tyr Met Glu Trp Val Arg Gln Ala Pro Gly
            180                 185                 190
```

```
aag ggg ctc gag tgg gtg gcc gct tcc agg aac aag gct aat gac tac    624
Lys Gly Leu Glu Trp Val Ala Ala Ser Arg Asn Lys Ala Asn Asp Tyr
        195                 200                 205 acc aca gag tac gcc gca agt gtt aaa ggc cgc ttt ata atc tcc cgc    672
Thr Thr Glu Tyr Ala Ala Ser Val Lys Gly Arg Phe Ile Ile Ser Arg
    210                 215                 220 gat gac tct aag aac tcc ttg tac ctt caa atg aat agt ctc aag aca    720
Asp Asp Ser Lys Asn Ser Leu Tyr Leu Gln Met Asn Ser Leu Lys Thr
225                 230                 235                 240 gaa gat aca gcg gta tac tac tgc gcc cgc gac tac tac gga tca agt    768
Glu Asp Thr Ala Val Tyr Tyr Cys Ala Arg Asp Tyr Tyr Gly Ser Ser
                245                 250                 255 tat tgg tac ttc gat gtt tgg aga gct ggc aca ctt gtg act gtc agc    816
Tyr Trp Tyr Phe Asp Val Trp Arg Ala Gly Thr Leu Val Thr Val Ser
            260                 265                 270 agt ctt gat cct aaa tcc tct gac aag acc tat acc tgc cca cct tgt    864
Ser Leu Asp Pro Lys Ser Ser Asp Lys Thr Tyr Thr Cys Pro Pro Cys
        275                 280                 285 ccc gcc cca gaa ctt ctg ggt ggc cca tcc gtg ttt ctg ttc cca cca    912
Pro Ala Pro Glu Leu Leu Gly Gly Pro Ser Val Phe Leu Phe Pro Pro
    290                 295                 300 aag cca aag gat aca ctc atg atc tct cgc act ccg gaa gtc acg tgc    960
Lys Pro Lys Asp Thr Leu Met Ile Ser Arg Thr Pro Glu Val Thr Cys
305                 310                 315                 320 gtc gtg gtt gat gtg tca cac gag gac ccg gag gtc aaa ttc aat tgg   1008
Val Val Val Asp Val Ser His Glu Asp Pro Glu Val Lys Phe Asn Trp
                325                 330                 335 tac gtg gac gga gtc gag gtg cac aac gcc aag aca aag cca cgc gaa   1056
Tyr Val Asp Gly Val Glu Val His Asn Ala Lys Thr Lys Pro Arg Glu
            340                 345                 350 gag cag tac aac agc acg tat aga gta gtg agc gtg ctg aca gtg ctc   1104
Glu Gln Tyr Asn Ser Thr Tyr Arg Val Val Ser Val Leu Thr Val Leu
        355                 360                 365 cac cag gat tgg ctt aac ggt aag gaa tac aag tgt aag gtc tcc aac   1152
His Gln Asp Trp Leu Asn Gly Lys Glu Tyr Lys Cys Lys Val Ser Asn
    370                 375                 380 aaa gct ctt cct gct cca ata gaa aag acc att tca aag gcc aag ggg   1200
Lys Ala Leu Pro Ala Pro Ile Glu Lys Thr Ile Ser Lys Ala Lys Gly
385                 390                 395                 400 caa cct cga gaa ccc cag gtg tac acg ctg cct ccc agc cga gag gag   1248
Gln Pro Arg Glu Pro Gln Val Tyr Thr Leu Pro Pro Ser Arg Glu Glu
                405                 410                 415 atg acc aag aac caa gta agt ctg aca tgc ctt gtc aaa ggg ttc tac   1296
Met Thr Lys Asn Gln Val Ser Leu Thr Cys Leu Val Lys Gly Phe Tyr
            420                 425                 430 ccc tca gac atc gcc gtg gaa tgg gaa agc aac ggt caa ccc gaa aac   1344
Pro Ser Asp Ile Ala Val Glu Trp Glu Ser Asn Gly Gln Pro Glu Asn
        435                 440                 445 aat tac aag aca acg cca ccg gta ctc gat tcc gat ggt tcc ttt ttt   1392
Asn Tyr Lys Thr Thr Pro Pro Val Leu Asp Ser Asp Gly Ser Phe Phe
    450                 455                 460 ctg tac tcc aaa ctc acg gtg gac aag agt cga tgg cag cag gga aac   1440
Leu Tyr Ser Lys Leu Thr Val Asp Lys Ser Arg Trp Gln Gln Gly Asn
465                 470                 475                 480 gtt ttc tcc tgt tcc gtg atg cac gaa gca ctg cac aat cac tat acc   1488
Val Phe Ser Cys Ser Val Met His Glu Ala Leu His Asn His Tyr Thr
                485                 490                 495 cag aag tca ctg agt ttg agc cct ggc aaa gga ggg ggc gga tca cat   1536
Gln Lys Ser Leu Ser Leu Ser Pro Gly Lys Gly Gly Gly Gly Ser His
            500                 505                 510
```

-continued

```
cat cac cat cac cat taa                                          1554
His His His His His
            515

<210> SEQ ID NO 4
<211> LENGTH: 517
<212> TYPE: PRT
<213> ORGANISM: Artificial Sequence
<220> FEATURE:
<223> OTHER INFORMATION: Synthetic Construct

<400> SEQUENCE: 4

Met Glu Thr Asp Thr Leu Leu Leu Trp Val Leu Leu Trp Val Pro
1               5                   10                  15

Gly Ser Thr Gly Asp Ala Ala Asp Ile Val Met Thr Gln Ser Pro Asp
                20                  25                  30

Ser Leu Ala Val Ser Leu Gly Glu Arg Ala Thr Ile Asn Cys Thr Ala
            35                  40                  45

Ser Glu Ser Leu Tyr Ser Ser Lys His Val His Tyr Leu Ala Trp Tyr
        50                  55                  60

Gln Gln Lys Pro Gly Gln Pro Pro Lys Leu Leu Ile Tyr Gly Ala Ser
65                  70                  75                  80

Asn Arg Tyr Ile Gly Val Pro Asp Arg Phe Ser Gly Ser Gly Ser Gly
                85                  90                  95

Thr Asp Phe Thr Leu Thr Ile Ser Ser Leu Gln Ala Glu Asp Val Ala
            100                 105                 110

Val Tyr Tyr Cys Ala Gln Phe Tyr Ser Tyr Pro Leu Thr Phe Gly Gly
        115                 120                 125

Gly Thr Lys Val Glu Ile Lys Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Pro Gly Gly Ser Leu Arg Leu Ser Cys Ala Ala Ser Gly
                165                 170                 175

Phe Thr Phe Ser Asp Phe Tyr Met Glu Trp Val Arg Gln Ala Pro Gly
            180                 185                 190

Lys Gly Leu Glu Trp Val Ala Ala Ser Arg Asn Lys Ala Asn Asp Tyr
        195                 200                 205

Thr Thr Glu Tyr Ala Ala Ser Val Lys Gly Arg Phe Ile Ile Ser Arg
    210                 215                 220

Asp Asp Ser Lys Asn Ser Leu Tyr Leu Gln Met Asn Ser Leu Lys Thr
225                 230                 235                 240

Glu Asp Thr Ala Val Tyr Tyr Cys Ala Arg Asp Tyr Tyr Gly Ser Ser
                245                 250                 255

Tyr Trp Tyr Phe Asp Val Trp Arg Ala Gly Thr Leu Val Thr Val Ser
            260                 265                 270

Ser Leu Asp Pro Lys Ser Ser Asp Lys Thr Tyr Thr Cys Pro Pro Cys
        275                 280                 285

Pro Ala Pro Glu Leu Leu Gly Gly Pro Ser Val Phe Leu Phe Pro Pro
    290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350
```

-continued

Glu Gln Tyr Asn Ser Thr Tyr Arg Val Val Ser Val Leu Thr Val Leu
            355                 360                 365

His Gln Asp Trp Leu Asn Gly Lys Glu Tyr Lys Cys Lys Val Ser Asn
    370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Glu Glu
                405                 410                 415

Met Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
    450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Lys Gly Gly Gly Ser His
            500                 505                 510

His His His His His
        515

<210> SEQ ID NO 5
<211> LENGTH: 5
<212> TYPE: PRT
<213> ORGANISM: Artificial Sequence
<220> FEATURE:
<223> OTHER INFORMATION: Peptide Linker

<400> SEQUENCE: 5

Gly Gly Gly Gly Ser
1               5

<210> SEQ ID NO 6
<211> LENGTH: 7
<212> TYPE: PRT
<213> ORGANISM: Artificial Sequence
<220> FEATURE:
<223> OTHER INFORMATION: VH CDR1

<400> SEQUENCE: 6

Gly Phe Thr Phe Ser Asp Phe
1               5

<210> SEQ ID NO 7
<211> LENGTH: 8
<212> TYPE: PRT
<213> ORGANISM: Artificial Sequence
<220> FEATURE:
<223> OTHER INFORMATION: VH CDR2

<400> SEQUENCE: 7

Arg Asn Lys Ala Asn Asp Tyr Thr
1               5

<210> SEQ ID NO 8
<211> LENGTH: 16
<212> TYPE: PRT
<213> ORGANISM: Artificial Sequence
<220> FEATURE:
<223> OTHER INFORMATION: VH CDR3

<400> SEQUENCE: 8

Cys Ala Arg Asp Tyr Tyr Gly Ser Ser Tyr Trp Tyr Phe Asp Val Trp
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: VL CDR1

<400> SEQUENCE: 9

Thr Ala Ser Glu Ser Leu Tyr Ser Ser Lys His Lys Val His Tyr Leu
1               5                   10                  15

Ala

<210> SEQ ID NO 10
<211> LENGTH: 7
<212> TYPE: PRT
<213> ORGANISM: Artificial Sequence
<220> FEATURE:
<223> OTHER INFORMATION: VL CDR2

<400> SEQUENCE: 10

Gly Ala Ser Asn Arg Tyr Ile
1               5

<210> SEQ ID NO 11
<211> LENGTH: 10
<212> TYPE: PRT
<213> ORGANISM: Artificial Sequence
<220> FEATURE:
<223> OTHER INFORMATION: VL CDR3

<400> SEQUENCE: 11

Cys Ala Gln Phe Tyr Ser Tyr Pro Leu Thr
1               5                   10

<210> SEQ ID NO 12
<211> LENGTH: 16
<212> TYPE: PRT
<213> ORGANISM: Artificial Sequence
<220> FEATURE:
<223> OTHER INFORMATION: VL CDR1-humanized

<400> SEQUENCE: 12

Thr Ala Ser Glu Ser Leu Tyr Ser Ser Lys His Val His Tyr Leu Ala
1               5                   10                  15

<210> SEQ ID NO 13
<211> LENGTH: 1587
<212> TYPE: DNA
<213> ORGANISM: Artificial Sequence
<220> FEATURE:
<223> OTHER INFORMATION: Chimeric E06scFv-human IgG1-Fc antibody
      sequence
<220> FEATURE:
<221> NAME/KEY: CDS
<222> LOCATION: (1)..(1587)

<400> SEQUENCE: 13 atg gag aca gac aca ctc ctg cta tgg gta ctg ctg ctc tgg gtt cca      48
Met Glu Thr Asp Thr Leu Leu Leu Trp Val Leu Leu Leu Trp Val Pro
1               5                   10                  15

```
ggt tcc act ggt gac gcg gcc cag ccg gcc agg cgc gcc gta cga agc      96
Gly Ser Thr Gly Asp Ala Ala Gln Pro Ala Arg Arg Ala Val Arg Ser
             20                  25                  30 tta gac att gtg atg act cag tct cca tct tcc ctt tct gtg tca gca     144
Leu Asp Ile Val Met Thr Gln Ser Pro Ser Ser Leu Ser Val Ser Ala
             35                  40                  45 ggt aag aag gtc acc att agt tgc acg gcc agt gag agc ctt tat tca     192
Gly Lys Lys Val Thr Ile Ser Cys Thr Ala Ser Glu Ser Leu Tyr Ser
         50                  55                  60 agc aaa cac aag gtg cac tac ttg gct tgg tac cag aag aaa cca gag     240
Ser Lys His Lys Val His Tyr Leu Ala Trp Tyr Gln Lys Lys Pro Glu
65                  70                  75                  80 caa tct cct aaa ctg ctg ata tac ggg gca tcc aac cga tac att ggg     288
Gln Ser Pro Lys Leu Leu Ile Tyr Gly Ala Ser Asn Arg Tyr Ile Gly
                 85                  90                  95 gtc cct gat cgc ttc aca ggc agt gga tct ggg aca gat ttc act ctg     336
Val Pro Asp Arg Phe Thr Gly Ser Gly Ser Gly Thr Asp Phe Thr Leu
            100                 105                 110 acc atc agc agt gta cag gtt gaa gac ctc aca cat tat tac tgt gca     384
Thr Ile Ser Ser Val Gln Val Glu Asp Leu Thr His Tyr Tyr Cys Ala
        115                 120                 125 cag ttt tac agc tat ccg ctc acg ttc ggt gct ggg acc aag ctg gaa     432
Gln Phe Tyr Ser Tyr Pro Leu Thr Phe Gly Ala Gly Thr Lys Leu Glu
130                 135                 140 atc aaa ggt ggt gga gga tca ggt gga ggt ggt tca gga ggt ggc gga     480
Ile Lys Gly Gly Gly Gly Ser Gly Gly Gly Gly Ser Gly Gly Gly Gly
145                 150                 155                 160 tcc gag gtg aag ctg gtg gag tct gga gga ggc ttg gta cag cct ggg     528
Ser Glu Val Lys Leu Val Glu Ser Gly Gly Gly Leu Val Gln Pro Gly
                165                 170                 175 ggt tct ctg aga ctc tcc tgt gca act tct ggg ttc acc ttc agt gat     576
Gly Ser Leu Arg Leu Ser Cys Ala Thr Ser Gly Phe Thr Phe Ser Asp
            180                 185                 190 ttc tac atg gag tgg gtc cgc cag gct cca ggg aag aga ctg gag tgg     624
Phe Tyr Met Glu Trp Val Arg Gln Ala Pro Gly Lys Arg Leu Glu Trp
        195                 200                 205 att gct gca agt aga aac aaa gct aat gat tat aca aca gag tac gct     672
Ile Ala Ala Ser Arg Asn Lys Ala Asn Asp Tyr Thr Thr Glu Tyr Ala
210                 215                 220 gac tct gtg aag ggt cgg ttc atc gtc tcc aga gac act tcc caa agc     720
Asp Ser Val Lys Gly Arg Phe Ile Val Ser Arg Asp Thr Ser Gln Ser
225                 230                 235                 240 atc ctc tac ctt cag atg aat gcc ctg aga gcc gag gac act gcc att     768
Ile Leu Tyr Leu Gln Met Asn Ala Leu Arg Ala Glu Asp Thr Ala Ile
                245                 250                 255 tat tac tgt gca aga gat tac tac ggt agt agc tac tgg tac ttc gat     816
Tyr Tyr Cys Ala Arg Asp Tyr Tyr Gly Ser Ser Tyr Trp Tyr Phe Asp
            260                 265                 270 gtc tgg ggc gca ggg acc acg gtc acc gtc tcc tct ctg gac ccg aag     864
Val Trp Gly Ala Gly Thr Thr Val Thr Val Ser Ser Leu Asp Pro Lys
        275                 280                 285 tct tct gac aaa act tac aca tgc cca ccg tgc cca gca cct gaa ctc     912
Ser Ser Asp Lys Thr Tyr Thr Cys Pro Pro Cys Pro Ala Pro Glu Leu
290                 295                 300 ctg ggg gga ccg tca gtc ttc ctc ttc ccc cca aaa ccc aag gac acc     960
Leu Gly Gly Pro Ser Val Phe Leu Phe Pro Pro Lys Pro Lys Asp Thr
305                 310                 315                 320 ctc atg atc tcc cgg acc cct gag gtc aca tgc gtg gtg gtg gac gtg    1008
Leu Met Ile Ser Arg Thr Pro Glu Val Thr Cys Val Val Val Asp Val
                325                 330                 335
```

```
agc cac gaa gac cct gag gtc aag ttc aac tgg tac gtg gac ggc gtg    1056
Ser His Glu Asp Pro Glu Val Lys Phe Asn Trp Tyr Val Asp Gly Val
        340                 345                 350 gag gtg cat aat gcc aag aca aag ccg cgg gag gag cag tac aac agc    1104
Glu Val His Asn Ala Lys Thr Lys Pro Arg Glu Glu Gln Tyr Asn Ser
355                 360                 365 acg tac cgt gtg gtc agc gtc ctc acc gtc ctg cac cag gac tgg ctg    1152
Thr Tyr Arg Val Val Ser Val Leu Thr Val Leu His Gln Asp Trp Leu
    370                 375                 380 aat ggc aag gag tac aag tgc aag gtc tcc aac aaa gcc ctc cca gcc    1200
Asn Gly Lys Glu Tyr Lys Cys Lys Val Ser Asn Lys Ala Leu Pro Ala
385                 390                 395                 400 ccc atc gag aaa acc atc tcc aaa gcc aaa ggg cag ccc cga gaa cca    1248
Pro Ile Glu Lys Thr Ile Ser Lys Ala Lys Gly Gln Pro Arg Glu Pro
                405                 410                 415 cag gtg tac acc ctg ccc cca tcc cgg gag gag atg acc aag aac cag    1296
Gln Val Tyr Thr Leu Pro Pro Ser Arg Glu Glu Met Thr Lys Asn Gln
            420                 425                 430 gtc agc ctg acc tgc ctg gtc aaa ggc ttc tat ccc agc gac atc gcc    1344
Val Ser Leu Thr Cys Leu Val Lys Gly Phe Tyr Pro Ser Asp Ile Ala
        435                 440                 445 gtg gag tgg gag agc aat ggg cag ccg gag aac aac tac aag acc acg    1392
Val Glu Trp Glu Ser Asn Gly Gln Pro Glu Asn Asn Tyr Lys Thr Thr
    450                 455                 460 cct ccc gtg ctg gac tcc gac ggc tcc ttc ttc ctc tac agc aag ctc    1440
Pro Pro Val Leu Asp Ser Asp Gly Ser Phe Phe Leu Tyr Ser Lys Leu
465                 470                 475                 480 acc gtg gac aag agc agg tgg cag cag ggg aac gtc ttc tca tgc tcc    1488
Thr Val Asp Lys Ser Arg Trp Gln Gln Gly Asn Val Phe Ser Cys Ser
                485                 490                 495 gtg atg cac gag gct ctg cac aac cac tac acg cag aag agc ctc tcc    1536
Val Met His Glu Ala Leu His Asn His Tyr Thr Gln Lys Ser Leu Ser
            500                 505                 510 ctg tct ccg ggt aaa ggt gga ggt gga tca cat cat cat cat cat cat    1584
Leu Ser Pro Gly Lys Gly Gly Gly Gly Ser His His His His His His
        515                 520                 525 taa                                                                 1587

<210> SEQ ID NO 14
<211> LENGTH: 528
<212> TYPE: PRT
<213> ORGANISM: Artificial Sequence
<220> FEATURE:
<223> OTHER INFORMATION: Synthetic Construct

<400> SEQUENCE: 14

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Asp Ile Val Met Thr Gln Ser Pro Ser Ser Leu Ser Val Ser Ala
        35                  40                  45

Gly Lys Lys Val Thr Ile Ser Cys Thr Ala Ser Glu Ser Leu Tyr Ser
    50                  55                  60

Ser Lys His Lys Val His Tyr Leu Ala Trp Tyr Gln Lys Lys Pro Glu
65                  70                  75                  80

Gln Ser Pro Lys Leu Leu Ile Tyr Gly Ala Ser Asn Arg Tyr Ile Gly
                85                  90                  95
```

Val Pro Asp Arg Phe Thr Gly Ser Gly Ser Gly Thr Asp Phe Thr Leu
            100                 105                 110

Thr Ile Ser Ser Val Gln Val Glu Asp Leu Thr His Tyr Tyr Cys Ala
        115                 120                 125

Gln Phe Tyr Ser Tyr Pro Leu Thr Phe Gly Ala Gly Thr Lys Leu Glu
    130                 135                 140

Ile Lys Gly Gly Gly Gly Ser Gly Gly Gly Gly Ser Gly Gly Gly Gly
145                 150                 155                 160

Ser Glu Val Lys Leu Val Glu Ser Gly Gly Leu Val Gln Pro Gly
                165                 170                 175

Gly Ser Leu Arg Leu Ser Cys Ala Thr Ser Gly Phe Thr Phe Ser Asp
        180                 185                 190

Phe Tyr Met Glu Trp Val Arg Gln Ala Pro Gly Lys Arg Leu Glu Trp
    195                 200                 205

Ile Ala Ala Ser Arg Asn Lys Ala Asn Asp Tyr Thr Thr Glu Tyr Ala
        210                 215                 220

Asp Ser Val Lys Gly Arg Phe Ile Val Ser Arg Asp Thr Ser Gln Ser
225                 230                 235                 240

Ile Leu Tyr Leu Gln Met Asn Ala Leu Arg Ala Glu Asp Thr Ala Ile
            245                 250                 255

Tyr Tyr Cys Ala Arg Asp Tyr Tyr Gly Ser Ser Tyr Trp Tyr Phe Asp
            260                 265                 270

Val Trp Gly Ala Gly Thr Thr Val Thr Val Ser Ser Leu Asp Pro Lys
    275                 280                 285

Ser Ser Asp Lys Thr Tyr Thr Cys Pro Pro Cys Pro Ala Pro Glu Leu
290                 295                 300

Leu Gly Gly Pro Ser Val Phe Leu Phe Pro Pro Lys Pro Lys Asp Thr
305                 310                 315                 320

Leu Met Ile Ser Arg Thr Pro Glu Val Thr Cys Val Val Val Asp Val
            325                 330                 335

Ser His Glu Asp Pro Glu Val Lys Phe Asn Trp Tyr Val Asp Gly Val
        340                 345                 350

Glu Val His Asn Ala Lys Thr Lys Pro Arg Glu Glu Gln Tyr Asn Ser
        355                 360                 365

Thr Tyr Arg Val Val Ser Val Leu Thr Val Leu His Gln Asp Trp Leu
    370                 375                 380

Asn Gly Lys Glu Tyr Lys Cys Lys Val Ser Asn Lys Ala Leu Pro Ala
385                 390                 395                 400

Pro Ile Glu Lys Thr Ile Ser Lys Ala Lys Gly Gln Pro Arg Glu Pro
            405                 410                 415

Gln Val Tyr Thr Leu Pro Pro Ser Arg Glu Glu Met Thr Lys Asn Gln
        420                 425                 430

Val Ser Leu Thr Cys Leu Val Lys Gly Phe Tyr Pro Ser Asp Ile Ala
        435                 440                 445

Val Glu Trp Glu Ser Asn Gly Gln Pro Glu Asn Asn Tyr Lys Thr Thr
    450                 455                 460

Pro Pro Val Leu Asp Ser Asp Gly Ser Phe Phe Leu Tyr Ser Lys Leu
465                 470                 475                 480

Thr Val Asp Lys Ser Arg Trp Gln Gln Gly Asn Val Phe Ser Cys Ser
            485                 490                 495

Val Met His Glu Ala Leu His Asn His Tyr Thr Gln Lys Ser Leu Ser
        500                 505                 510

-continued

```
Leu Ser Pro Gly Lys Gly Gly Gly Ser His His His His His
        515             520             525
```

ANTIBODIES TO OXIDIZED PHOSPHOLIPIDS

CROSS REFERENCE TO RELATED APPLICATIONS

This application is a continuation of U.S. application Ser. No. 14/770,160, filed Aug. 25, 2015, which claims priority under 35 U.S.C. § 371 to International Application No. PCT/US2014/018402, filed Feb. 24, 2014, which application claims priority under 35 U.S.C. § 119 from Provisional Application Ser. No. 61/769,154, filed Feb. 25, 2013, and Provisional Application Ser. No. 61/894,220, filed Oct. 22, 2013, the disclosures of which are incorporated herein by reference.

GOVERNMENT LICENSE RIGHTS

This invention was made with Government support under Grant Nos. HL086559 & HL088093, awarded by the National Institutes of Health. The Government has certain rights in the invention.

TECHNICAL FIELD

The disclosure provides humanized antibodies and single chain variable region (scFv) that bind to oxidized phospholipids. The disclosure relates to methods and compositions to treat patients with antibodies and scFv's that have the binding specificity of an E06 antibody with aortic stenosis.

BACKGROUND

Calcific aortic stenosis is a fairly common disorder in adults (3% of the population), for which there is no current medical therapy. The only treatment is aortic valve replacement, but this is only done when end stage disease occurs and there is a potential for mortality and morbidity. There is also no treatment to delay or prevent progression of aortic valve stenosis.

Monoclonal antibodies have become an important class of therapeutic proteins. However, foreign immunoglobulins used in humans can elicit an anti-globulin response which may interfere with therapy or cause allergic or immune complex hypersensitivity. To avoid this problem, a monoclonal antibody may be "humanized," and this is typically carried out by CDR grafting.

SUMMARY

The disclosure provides an antibody or antibody fragment that recognizes and binds to a phosphocholine headgroup of an oxidized phospholipid, wherein the antibody or antibody fragment comprises a variable heavy chain ($V_H$) domain and/or a variable light chain ($V_L$) domain, and wherein (a) the $V_H$ domain comprises an amino acid sequence that includes one, two or three complementarity determining regions (CDRs) selected from the group consisting of: SEQ ID NO:6 and sequence that are at least 95%, 96%, 97%, 98%, 99% or 99.9% identical to SEQ ID NO:6; SEQ ID NO:7 and sequence that are at least 95%, 96%, 97%, 98%, 99% or 99.9% identical to SEQ ID NO:7; and SEQ ID NO:8 and sequence that are at least 95%, 96%, 97%, 98%, 99% or 99.9% identical to SEQ ID NO:8; and (b) the $V_L$ domain comprises an amino acid sequence that includes one, two or three complementarity determining regions (CDRs) selected from the group consisting of: SEQ ID NO:9 or 12 and sequence that are at least 95%, 96%, 97%, 98%, 99% or 99.9% identical to SEQ ID NO:9 or 12; SEQ ID NO:10 and sequence that are at least 95%, 96%, 97%, 98%, 99% or 99.9% identical to SEQ ID NO:10; and SEQ ID NO:11 and sequence that are at least 95%, 96%, 97%, 98%, 99% or 99.9% identical to SEQ ID NO:11. In one embodiment, the $V_H$ domain comprises an amino acid sequence that includes CDRs comprising SEQ ID NO:6, 7 and 8, and/or the $V_L$ domain comprises an amino acid sequence that includes CDRs comprising SEQ ID NO:9, 10 and 11, or SEQ ID NO:10, 11 and 12. In another embodiment of any of the foregoing, the antibody or antibody fragment is selected from the group consisting of: (a) an antibody or scFv with heavy and light chain domains comprising the complementarity determining regions of SEQ ID NO:6, 7, 8, 9, 10 and 11; and (b) an antibody or scFv with heavy and light chain domains comprising the complementarity determining regions of SEQ ID NO:6, 7, 8, 10, 11 and 12. In another embodiment of any of the foregoing, the heavy and light chain domains are linked to an Fc region, typically through a linker/hinge domain. In another embodiment of the foregoing, an antibody fragment comprising a single chain variable fragment ("scFv") that recognizes a phosphocholine headgroup of an oxidized phospholipid is provided. In one embodiment, the scFv is soluble under physiological conditions. In another embodiment, the scFv is murine. In yet another embodiment, the scFv is humanized. In yet further embodiments of the foregoing the scFv comprises a light-chain variable region having a sequence that is at least 95% identical to the sequence as set forth in SEQ ID NO:2 from amino acid 34 to about amino acid 146. In a further embodiment, the scFv comprises a heavy chain variable region having a sequence that is at least 95% identical to the sequence as set forth in SEQ ID NO:2 from about amino acid 162 to about amino acid 284. In yet another embodiment, the scFv comprises a light-chain variable region having a sequence that is at least 95% identical to the sequence as set forth in SEQ ID NO:4 from amino acid 24 to about amino acid 135. In a further embodiment, the scFv comprises a heavy chain variable region having a sequence that is at least 95% identical to the sequence as set forth in SEQ ID NO:4 from about amino acid 151 to about amino acid 273. In another embodiment, the scFv comprises a sequence that is at least 95% identical to the sequence as set forth in SEQ ID NO:2. In another embodiment, the scFv comprises a sequence that is at least 95% identical to the sequence as set forth in SEQ ID NO:4 from amino acid 1 to about amino acid 273.

The disclosure also provides an antibody comprising a variable light chain and variable heavy chain of the foregoing embodiments. In one embodiment, the antibody is chimeric. In a further embodiment, the variable light chain and variable heavy chain are non-human and an Fc region is human or humanized. In yet another embodiment, the variable light chain and variable heavy chain are human or humanized and the Fc region is non-human. In another embodiment, the antibody is humanized. In a further embodiment, the antibody comprises a sequence that is at least 95% identical to a sequence as set forth in SEQ ID NO:4.

The disclosure also provides a polynucleotide that encodes an antibody, antibody fragment, variable light chain, variable heavy chain or scFv as described above in any of the foregoing embodiments. In one embodiment, the polynucleotide comprises a sequence that is at least 95% identical to SEQ ID NO:1 or 3 and encodes a polypeptide that has the binding specificity of an E06 antibody.

The disclosure also provides a vector comprising a polynucleotide encoding any of the antibodies, antibody fragments or scFv's described above.

The disclosure also provides a host cell transformed with a polynucleotide encoding any of the antibodies, antibody fragments or scFv's described above.

The disclosure also provides a host cell transformed with a vector comprising a polynucleotide encoding any of the antibodies, antibody fragments or scFv's described above.

The disclosure also provides a transgenic animal or plant, comprising a polynucleotide encoding any of the antibodies, antibody fragments or scFv's described above.

The disclosure also provide a method of treating a subject with an inflammatory disease, disorder or condition or a disease or condition associated with oxidized phospholipids by administering an antibody, antibody fragment, or scFv as described above in any of the foregoing embodiments.

The disclosure also provides a method of treating or preventing calcific aortic stenosis (CAS) comprising administering an antibody, antibody fragment, or scFv as described above in any of the foregoing embodiments to a subject having or at risk of having CAS.

The disclosure also provides for the use of a single chain variable fragment ("scFv") of a monoclonal antibody which binds to the phosphocholine headgroup of oxidized phospholipids (OxPL) or humanized version thereof to treat calcific aortic stenosis (CAS). OxPL are highly proinflammatory molecules and also form ligands on oxidized LDL (OxLDL) that mediate uptake of OxLDL by macrophages. Accordingly, the disclosure further provides that the scFv's disclosed herein which bind to OxLDL and prevent its binding and uptake by macrophage scavenger receptors and also binds to OxPL molecules, as for example on apoptotic cells, and thus inhibits their proinflammatory effects.

Additionally, the scFv of the disclosure can be used to generate transgenic animals which express scFv's disclosed herein. In a particular embodiment, the transgenic animal expresses scFv's or antibodies of the disclosure from hepatocytes and/or macrophages. In a further embodiment, scFv's or antibodies disclosed herein can be used as anti-inflammatory and/or anti-atherosclerosis therapeutic agents.

The disclosure provides a fully functional and unique E06 single chain antibody (E06-scFv). This scFv retains all the biological properties of the parent antibody including the ability to bind to an anti-idiotypic antibody. This has been used to develop high expressing transgenic mice that express the scFv both in the liver and in macrophages. These mice have been bred into the LDL-receptor negative background. Feeding LDLr mice a high cholesterol diet induces atherosclerosis and also generalized inflammation as indicated by elevated plasma SAA. The presence of the E06-scFv reduces the extent of atherosclerosis by 55% over a 16 week time period and dramatically reduces plasma SAA. Cholesterol accumulation in peritoneal macrophages is reduced by 50% and inflammatory gene expression is reduced as well. Livers from chol-fed mice show marked steatosis and presence of OxPL, which is dramatically reduced by the E06-scFv. In addition, bone marrow transplantation from the transgenic mice to LDLr mice also confers sufficient E06-scFv to provide atheroprotection. As the E06-scFv lacks any functional properties of antibodies other than to target OxPL, these data demonstrate that OxPL are very proinflammatory in multiple organs, and proatherogenic, and that the E06-scFv can dramatically ameliorate their proinflammatory and proatherogenic properties.

The E06-scFv, and/or a humanized IgG version of the antibody of the disclosure can be developed for use as an anti-inflammatory agent, and as an anti-atherosclerotic agent, for use in humans in a variety of settings.

Further, the availability of a transgenic mouse model expressing this antibody allows for in depth preclinical testing of any one of a myriad of potential applications. Interventions can be done on these mice to test the impact of the E06-scFv and/or the mice can be bred into other backgrounds. In addition, because macrophages express the transgene, bone marrow transplantation from the transgenic mice to a wide variety of other murine models may be sufficient to allow testing of impact of the E06-scFv in a variety of settings, without the need to do extensive breeding. In addition, similar transgenic mice, but ones in which an Fc portion has been added are described, and thus the mice will express an IgG equivalent. This will allow comparison of the effects of an "intact" IgG vs. those of the scFv alone.

The E06-scFv or IgG equivalent can be used for many possible therapeutic uses. It can be used in patients with acute respiratory distress, or in any acute fulminating pneumonias. Likely it would be equally valuable in other acute inflammatory settings. The data presented below shows that the antibody inhibits an immunologically induced arthritis model and would be of great benefit without immunological suppression. It can be useful in patients with acute hepatitis, or with NASH and metabolic syndrome. They antibodies or fragments thereof of the disclosure can be used in applications and diseases where OxPL have been shown to play a role. Furthermore, E06 also binds the PC present on the cell wall of *S. pneumonia* (and other pathogens) and in vivo provides optimal protection to mice against lethal pneumococcal disease. Accordingly, the antibody or fragments thereof of the disclosure can be useful for patients with severe pneumococcal disease as well.

The scFv can also play a major role in cardiovascular disease. For example, material trapped in distal protection devices following PCI procedures on human coronary lesions during interventional procedures and using immunological and mass spectrometry techniques, shown that there are abundant OxPL released. Such OxPL are abundant in late stage "vulnerable" plaques. A coinjection of the anti-OxPL antibody could bind and block downstream proinflammatory or vasoactive effects. Similarly, use of the antibody in patients with acute coronary syndromes or with "crescendo angina" may similarly be of benefit. One can envision chronic use (e.g., 1-2 years) in high risk patients, e.g. those immediately post MI, realizing that in such populations multiple vulnerable plaque lesions are likely present aside from the one(s) that caused the acute event. This may be equally applicable to acute stroke; inhibiting products of lipid peroxidation ameliorates stroke damage in a murine model. Furthermore, the scFv of the disclosure has the ability to lower inflammation systemically.

The scFv-E06 and antibodies of the disclosure binds to OxPL and blocks their proinflammatory effects. One could infuse the antibody or other OxPL-targeted therapeutic agent to patients with early or late manifestation of aortic stenosis or in those who have bicuspid aortic valves and the agent would bind to the OxPL in the valve and prevent their pro-inflammatory effects, which would reduce progression of valve stenosis. As noted in the transgenic model, the presence of the E06-scFv dramatically inhibited aortic stenosis and malfunction in Ldlr$^{-/-}$ mice fed a high cholesterol diet. The development of a transgenic murine model provides a mechanism to allow preclinical testing of the impact of the E06-scFv on an acute or chronic disease process. The transgenic mice can be subjected to a given inflammatory event, for example, by provoking acute respiratory distress by bronchial installation of offending agent, such as acid, and the response compared in the transgenic mouse vs that in a control. The impact of the antibody can be tested in more chronic settings by breeding the transgenic mouse into the appropriate experimental murine model. For example, the E06-scFv transgenic mouse were bred in the Ldlr$^{-/-}$ mouse background, which develops atherosclerosis when fed a high cholesterol diet. In addition, because the eE06-scFv is synthesized and secreted by macrophages in the mouse model, one could transfer bone marrow from the E06-scFv transgenic mice to a recipient, and evaluate the expression of the antibody on a biological process in those mice, without the need for extensive breeding. As noted above this allows direct study of the impact of the scFv on disease endpoints and also provides murine models to allow study of the mechanisms by which the antibody achieves its biological effects.

The antibody or therapeutic fragments thereof can be given to patients with any level of aortic stenosis (with either tricuspid or bicuspid aortic valves) to prevent progression and obviate the need for surgical replacement and all the risk involved with this, either acutely during the operation or later with anticoagulation that is needed and repeat surgery. In addition, the fact that the E06-scFc could be expressed from macrophages suggests the possibility that such a strategy could be used in humans to provide sustained systemic levels of the E06-scFv in humans. Finally, a humanized IgG version of this antibody can be developed for use as an anti-inflammatory agent, and as an anti-atherosclerotic agent in humans in a variety of settings.

The E06-scFv has great potential for clinical application. The availability of a transgenic mouse expressing a fully functional scFv (and intended model expressing an IgG equivalent) provides an obvious and highly efficient path forward for preclinical testing of possible clinical applications.

DESCRIPTION OF DRAWINGS

FIG. 16 demonstrates the expression of E06-scFv in aortic lesion area of transgenic mice. Cross sections at the aortic valve were stained with biotinylated AB1-2 showing E06-scFv immune complex in the lesions.

FIG. 20 shows the nucleotide (SEQ ID NO:1) and amino acid (SEQ ID NO:2) sequence and annotations of an scFv of the disclosure.

FIG. 21 shows the nucleotide (SEQ ID NO:13) and amino acid (SEQ ID NO:14) sequence and annotations of a chimeric antibody of the disclosure.

FIG. 22 shows the nucleotide (SEQ ID NO:3) and amino acid (SEQ ID NO:4) sequence and annotations of a humanized antibody of the disclosure.

DETAILED DESCRIPTION

Figure 1A:
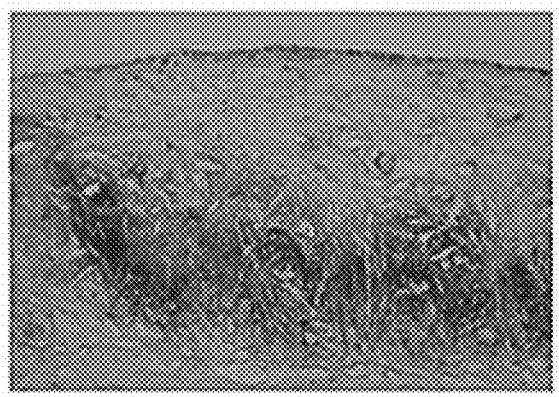
FIG. 1A-E provides images of immunochemistry studies from various tissues or cells that express oxidation epitopes including (A) atherosclerosis, (B) rheumatoid arthritis, (C) apoptotic cells, (D) brain lesion, and (E) lung tissue with acute injuries.
Figure 1B:
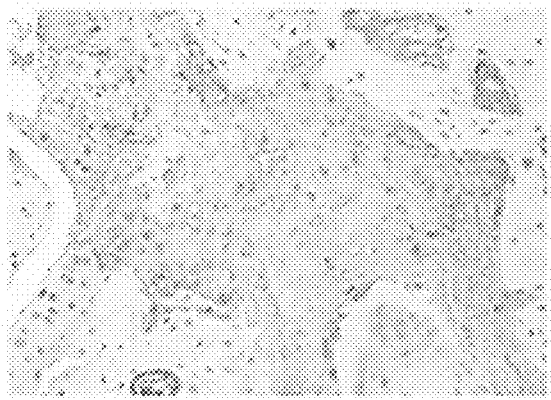
Figure 1C:
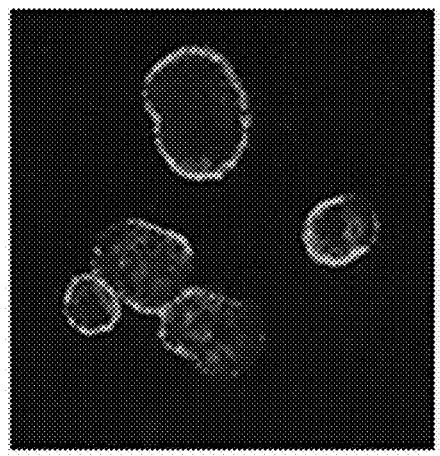
Figure 1D:
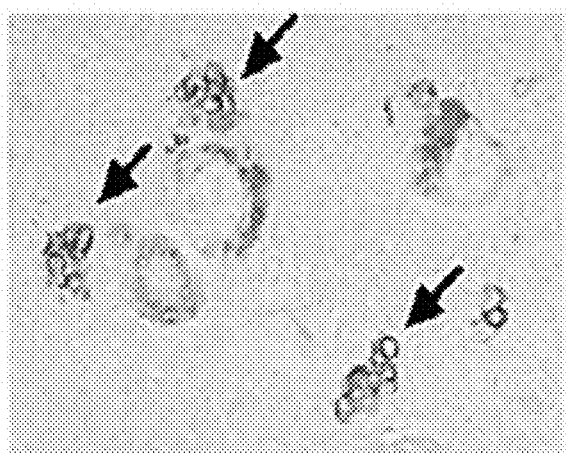
Figure 1E:
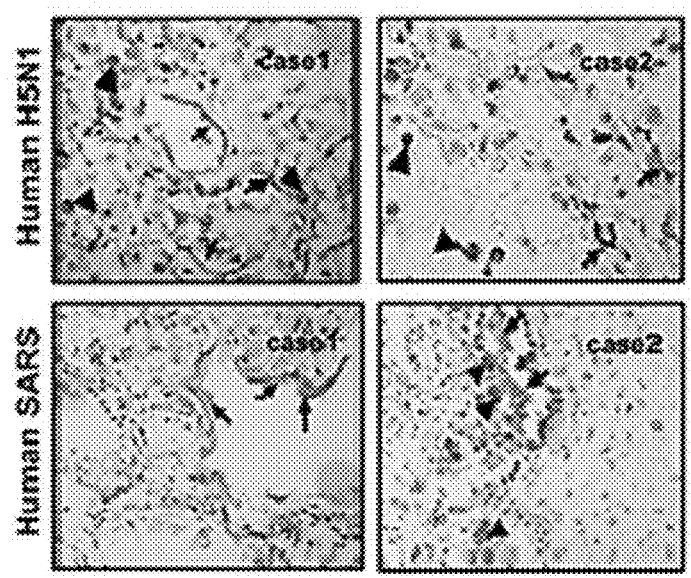
Figure 2A:
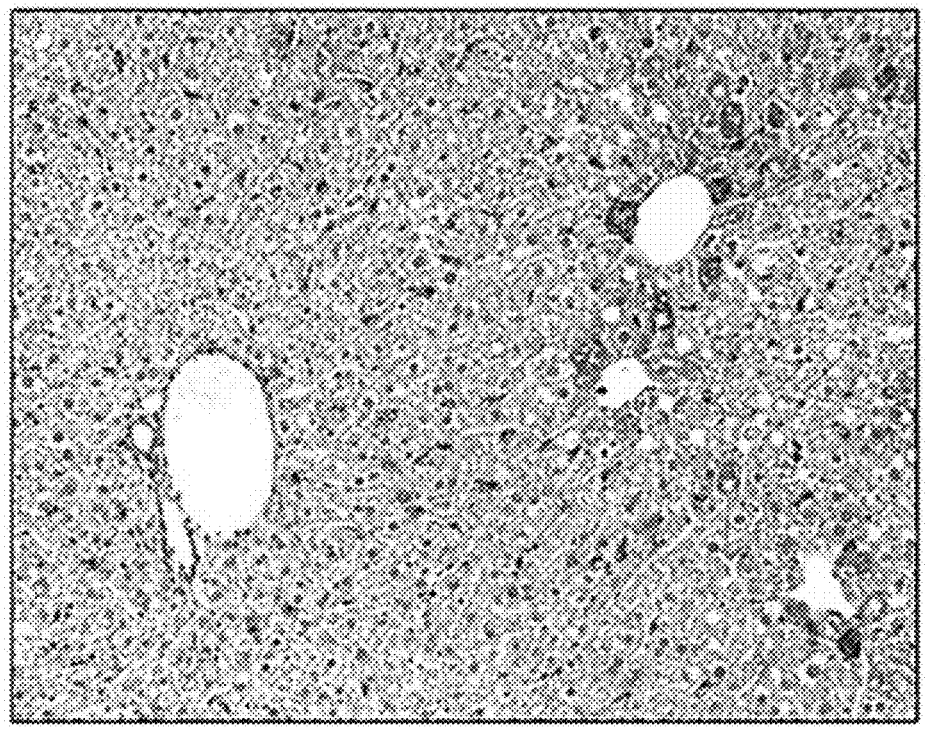
FIG. 2A-B presents images of a liver of mouse that was fed high fat diet (A) and chow-fed (B). Both images were generated by staining with IgM neutralizing antibody (Nab) E06 ("E06 antibody").
Figure 2B:
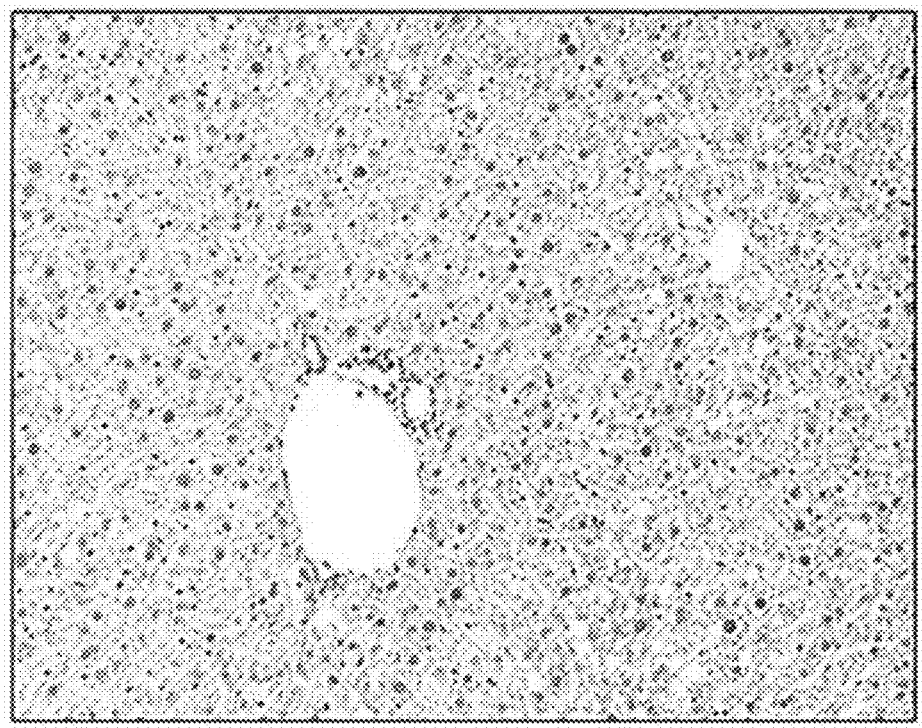

As used herein and in the appended claims, the singular forms "a," "and," and "the" include plural referents unless the context clearly dictates otherwise. Thus, for example, reference to a "single-chain variable fragment" or "scFv" includes a plurality of single-chain variable fragments and reference to "oxidized phospholipid" includes reference to one or more oxidized phospholipids and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Innate natural antibodies (NAbs) provide the first line of host defense against common oxidation-specific epitopes (OSE) on endogenous neo-epitopes (OxLDL and apoptotic cells) and exogenous epitopes of pathogens, and maintain host homeostasis. OSEs are ubiquitous, formed in many inflammatory tissues, including atherosclerotic lesions, and are a major target of IgM NAbs. The prototypic IgM NAb E06, which binds the phosphocholine (PC) headgroup in oxidized phospholipids (OxPL), blocks uptake of OxLDL by macrophages. To determine the impact in vivo of sustained titers of E06, transgenic mice expressing a single-chain antibody fragment (scFv) of E06 were generated. The E06-scFv was expressed in vivo, using the apoE promoter, and used to generate transgenic mice (Tg) in Ldlr$^{-/-}$ background. The E06-scFv was secreted into the plasma, bound to PC-BSA and OxLDL, and achieved sufficient plasma levels to inhibit binding of OxLDL to macrophages in culture at high plasma dilution.

The extent of atherosclerosis in male Ldlr$^{-/-}$ and E06-scFv-Tg Ldlr$^{-/-}$ mice fed 1% cholesterol diet for 16 weeks (n=10-12) was compared. Plasma cholesterol levels were similar. In the Tg mice, en face lesion area was decreased 57% (8.28% vs 3.54%, p<0.02) and lesion area at aortic root decreased 55%. Peritoneal macrophages from E06-scFv-Tg mice had 49% less cholesterol, consistent with decreased OxLDL uptake, and also had decreased inflammatory gene expression. Plasma SAA (serum amyloid A) was also reduced 32%, consistent with generalized decreased inflammation. As macrophages also secreted E06-scFv, bone marrow transplantation (BMT) was performed from E06-scFv-Tg into irradiated Ldlr$^{-/-}$ recipients (n=10-12): this also decreased aortic root lesions 31% compared to BMT with wt mice donors, even though plasma E06-scFv titers were only 10% of that in Tg mice. Hepatic steatosis was also dramatically decreased in Tg mice as was hepatic inflammatory gene expression.

When these mice are bred into LDL-receptor negative (Ldlr$^{-/-}$) mice that develop atherosclerosis when fed a high cholesterol diet, the presence of the scFv dramatically inhibits the development of atherosclerosis and also inhibits inflammation in the whole body and in the liver.

The E06-scFv lacks functional effects of an intact antibody other than the ability to bind OxPL and inhibit OxLDL uptake in macrophages. Thus, these data demonstrate that OxPL are profoundly proinflammatory and proatherogenic, which E06 counteracts in vivo. Taken together, these studies suggest that E06-scFv has great potential in preventing the progression of atherosclerosis and inflammation.

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments. An antibody can be human, humanized and/or affinity matured.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. PNAS (USA) 95:652-656 (1998).

"Antibody fragments" comprise only a portion of an intact antibody, wherein the portion typically retains at least one, more commonly most or all, of the functions normally associated with that portion when present in an intact antibody. Examples of antibody fragments include Fab, Fab', $F(ab')_2$, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment.

An "antigen" is a predetermined antigen to which an antibody can selectively bind. The target antigen may be polypeptide, carbohydrate, nucleic acid, lipid, hapten or other naturally occurring or synthetic compound. In one embodiment, of the disclosure an antigen is an OxPL.

The term "anti-OxPL antibody" or "an antibody that binds to OxPL" refers to an antibody that is capable of binding OxPL with sufficient affinity such that the antibody is useful as a diagnostic and/or therapeutic agent in targeting OxPL. In some embodiments of the disclosure an anti-OxPL antibody has the same or a similar binding specificity and $K_d$ as the E06 antibody.

A "blocking" antibody or an "antagonist" antibody is one which inhibits or reduces biological activity of the antigen it binds. Certain blocking antibodies or antagonist antibodies substantially or completely inhibit the biological activity of the antigen.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass), which are bound to their cognate antigen. To assess complement activation, a CDC assay, e.g., as described in Gazzano-Santoro et al., J. Immunol. Methods 202:163 (1996), may be performed. Polypeptide variants with altered Fc region amino acid sequences (polypeptides with a variant Fc region) and increased or decreased Clq binding capability are described, e.g., in U.S. Pat. No. 6,194,551 B1 and WO 1999/51642. See also, e.g., Idusogie et al. J. Immunol. 164: 4178-4184 (2000).

A "disorder" or "disease" is any condition that would benefit from treatment with a substance/molecule or method of the disclosure. This includes chronic and acute disorders or diseases including those pathological conditions which predispose the mammal to the disorder in question. Non-limiting examples of disorders to be treated herein include cardiovascular disease and stenosis.

Antibody "effector functions" refer to those biological activities attributable to the Fc region of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" as used herein refers to the C-terminal region of an immunoglobulin heavy chain, including native sequence Fc regions and variant Fc regions.

A "functional Fc region" possesses an "effector function" of a native sequence Fc region. Such effector functions generally require the Fc region to be combined with a binding to domain (e.g., an antibody variable domain) and can be assessed using various assays as disclosed, for example, in definitions herein.

A "native sequence Fc region" comprises an amino acid sequence that is identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

Fc receptor also include the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

Binding to human FcRn in vivo and serum half-life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. J. Biol. Chem. 9(2):6591-6604 (2001).

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains have a free thiol group. F(ab')$_2$ antibody fragments originally were produced as pairs of Fab' fragments which have hinge cysteines between them. Other chemical couplings of antibody fragments are also known.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584). See also, for example, Li et al., Proc. Natl. Acad. Sci. USA, 103:3557-3562 (2006) regarding human antibodies generated via a human B-cell hybridoma technology.

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and typically more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. An isolated antibody includes the antibody in situ within recombinant cells since at least one component of the antibody's natural environment will not be present. Ordinarily, however, an isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

The "light chains" of antibodies (immunoglobulins) from any vertebrate species can be assigned to one of two clearly distinct types, called kappa (κ) and lambda (λ), based on the amino acid sequences of their constant domains.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier term "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody for purposes of this disclosure. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier term "monoclonal" indicates the character of the antibody as being obtained from a substantially homogeneous population of antibodies, and is not to be construed as requiring production of the antibody by any particular method. For example, the monoclonal antibodies to be used in accordance with the disclosure may be made by a variety of techniques, including, for example, the hybridoma method (e.g., Kohler and Milstein, Nature, 256: 495-97 (1975); Hongo et al., Hybridoma, 14 (3): 253-260

(1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA 81:6851-6855 (1984)). Chimeric antibodies include antibodies wherein the antigen-binding region of the antibody is derived from an antibody produced by, e.g., immunizing macaque monkeys with the antigen of interest.

"Oligonucleotide," as used herein, refers to short, typically single stranded polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

Oxidized phospholipids (OxPL) refer to phospholipids with a phosphocholine (PC) headgroup. OxPL are highly pro-inflammatory and proatherogenic. Phosphorylcholine, a polar head group on certain phospholipids, has been extensively implicated in cardiovascular disease. Reactive oxygen species generated during coronary inflammation causes the oxidation of low density lipoprotein (LDL) to generate oxidized LDL (oxLDL). In fact, cardiovascular diseases (CVD) such as atherosclerosis, unstable angina, or acute coronary syndrome have been shown to be associated with elevated plasma levels of oxLDL (Itabe and Ueda. 2007). LDL is a circulating lipoprotein particle that contains lipids with a PC polar head group and proteins, an apoB100 protein.

During oxidation of LDL PC containing neo-epitopes that are not present on unmodified LDL are generated. Newly exposed PC on oxLDL is recognized by scavenger receptors on macrophages, such as CD36, and the resulting macrophage-engulfed oxLDL proceeds towards the formation of proinflammatory foam cells in the vessel wall. Oxidized LDL is also recognized by receptors on endothelial cell surfaces and has been reported to stimulate a range of responses including endothelial dysfunction, apoptosis, and the unfolded protein response (Gora et al. 2010). PC neo-epitopes are also exposed on LDL following modification with phospholipase A2 or amine reactive disease metabolites, such as aldehydes generated from the oxidation of glycated proteins. These alternately modified LDL particles are also pro-inflammatory factors in CVD.

Antibodies towards phosphorylcholine (PC) have been shown to bind oxidized, or otherwise modified, LDL and block the pro-inflammatory activity of oxLDL in in vivo models or in vitro studies (Shaw et al. 2000; Shaw et al. 2001).

A "polynucleotide," or "nucleic acid," as used herein, refer to polymers of nucleotides of any length, and include DNA and RNA. The nucleotides can be deoxyribonucleotides, ribonucleotides, modified nucleotides or bases, and/or their analogs that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Single-chain Fv" or "scFv" antibody fragments comprise the $V_H$ and $V_L$ domains of antibody, wherein these domains are present in a single polypeptide chain. Generally, the scFv polypeptide further comprises a polypeptide linker between the $V_H$ and $V_L$ domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "substantially similar" or "substantially the same," as used herein, denotes a sufficiently high degree of similarity between two numeric values (for example, one associated with an antibody of the disclosure and the other associated with a reference/comparator antibody), such that one of skill in the art would consider the difference between the two values to be of little or no biological and/or statistical significance within the context of the biological characteristic measured by the values (e.g., $K_d$ values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., $K_d$ values). The difference between said two values is, for example, greater than about 10%, greater than about 20%, greater than about 30%, greater than about 40%, and/or greater than about 50% as a function of the value for the reference/comparator molecule.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions or hypervariable regions (CDRs or HVRs, used interchangeably herein) both in the light-chain and the heavy-chain variable domains. The more highly conserved portions of variable domains are called the framework (FR). The variable domains of native heavy and light chains each comprise four FR regions, largely adopting a (3-sheet configuration, connected by three HVRs, which form loops connecting, and in some cases forming part of, the (3-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and replicate along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$—$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993). Triabodies and tetrabodies are also described in Hudson et al., Nat. Med. 9:129-134 (2003).

A "variant Fc region" comprises an amino acid sequence which differs from that of a native sequence Fc region by virtue of at least one amino acid modification, typically one or more amino acid substitution(s). Typically, the variant Fc region has at least one amino acid substitution compared to a native sequence Fc region or to the Fc region of a parent polypeptide, e.g. from about one to about ten amino acid substitutions, and typically from about one to about five amino acid substitutions in a native sequence Fc region or in the Fc region of the parent polypeptide. The variant Fc region of a disclosure possesses at least about 80% homology with a native sequence Fc region and/or with an Fc region of a parent polypeptide, at least about 90% homology therewith, and typically at least about 95% homology therewith.

Calcific aortic valve stenosis (CAVS) is the common form of acquired valvular heart disease, present in 3% of the population over 75 years of age. While risk factors are similar for CAVS and atherosclerosis, ~50% of patients with CAVS do not have clinically significant cardiovascular disease (CVD), suggesting related but unique pathophysiology. Although surgical aortic valve replacement (SAVR) remains the gold standard treatment for most patients, at least one third of symptomatic patients with CAVS may not undergo SAVR. To fill this clinical need, transcatheter aortic valve replacement (TAVR) is increasingly being used, but overall survival remains modest due to the advanced age and other co-morbidities. With the aging of the population, the prevalence of CAVS will increase rapidly and portends medical, financial and ethical burdens to healthcare systems worldwide. Hence, identification of causal pathways mediating CAVS can provide novel targets for earlier therapy prior to end-stage disease. One of these pathways involves the lipoprotein (a) [Lp(a)], lipoprotein-associated phospholipase $A_2$ (Lp-$PLA_2$) and oxidized phospholipids (OxPL) axis.

Valvular calcification precedes the development of CAVS and is actively regulated. Oxidative stress, calcific nodules and inflammatory infiltrates play a significant role in CAVS and the accumulation of OxLDL is associated with increased inflammation and may potentiate calcification and matrix remodeling. Treatment of calcifying aortic smooth muscle cells with OxPL has been shown to stimulate expression of alkaline phosphatase and formation of cellular aggregates containing calcium mineral, characteristic features of osteoblastic differentiation. Recently, OxLDL and Lp(a) have been shown to bind monocyte chemoattractant protein-1 (MCP-1), which may play a role in attracting monocytes to subendothelial spaces.

There is currently no medical therapy to prevent or reduce the progression of CAVS in humans. Studies in hypercholesterolemic Ldlr$^{-/-}$ mice have shown that they develop CAVS and that lowering cholesterol earlier in the course of disease progression slows aortic stenosis, but if begun much later will not influence the extent of stenosis. Retrospective human studies have suggested statins are effective in reducing progression. However, prospective, randomized human trials, including SALTIRE (atorvastatin 80 mg/d), TASS (atorvastatin 20 mg/d), SEAS (simvastatin 40 mg/d plus ezetimibe 10 mg/d) and ASTRONOMER (rosuvastatin 40 mg/d), have shown no significant effect on CAVS progression. There are several possibilities for the negative results, including that treatment of elderly patients studied in these trials who already had moderate to heavily calcified valves at the end stage of the disease, were treated too late to influence disease outcomes. Therefore, therapeutic agents beyond standard lipid lowering therapy are needed to impact CAVS.

The above observations suggest that targeting Lp(a)-Lp-PLA$_2$-OxPL pathways may be a viable approach in mitigating CAVS. This can be done be several currently available approaches targeting Lp(a), including antisense oligonucleotides specifically directed to apo(a) of Lp(a) currently in Phase I trials, which lower Lp(a) levels >85%; inhibitors of Lp-PLA$_2$ such as darapladib currently being evaluated in Phase 3 trials in patients with acute coronary syndromes and stable coronary artery disease; and therapies to prevent oxidation of lipoproteins or minimize their pro-inflammatory effects, such as sufficient antioxidants, oxidation-specific antibodies targeting OxPL and other immunomodulatory agents. It also sets the stage for the discovery of new therapeutic agents.

Lp(a) is composed of apolipoprotein B-100 (apoB) covalently bound to apolipoprotein (a). Based on recent meta-analyses, genome wide association (GWAS) and Mendelian randomization studies, Lp(a) is now generally considered a causal risk factor for CVD. Recently, a GWAS study of multiple ethnic groups showed that genetic variation at the LPA gene locus, as manifested by snp rs10455872, was causally related to CAVS.

Lp(a) is pro-atherogenic due to its LDL moiety and through additional mechanisms mediated by apo(a). A key pro-inflammatory property of Lp(a) is the content of OxPL. Among lipoproteins, OxPL is predominantly found on Lp(a), with only small amounts on LDL and HDL. A large clinical database supports the hypothesis that the risk of Lp(a) is driven by its content of OxPL, mainly present on small apo(a) isoforms associated with high Lp(a) levels. Elevated levels of OxPL on apolipoproteins B-100 (OxPL/apoB) predict death, myocardial infarction and stroke, reclassify ~30% of patients to different risk categories, and reflect extent of CVD in multiple arterial beds.

Lp-PLA$_2$ hydrolyzes OxPL to yield a free oxidized fatty acid (OxFA) and lysophosphatidylcholine (LPC). Both the precursor (OxPL) and the 2 by-products of Lp-PLA$_2$ manifest pro-inflammatory effects. Clinical trials are being performed to assess whether inhibiting breakdown of OxPL with the Lp-PLA$_2$ inhibitor, darapladib, will improve clinical outcomes. Lp-PLA$_2$ is secreted by inflammatory cells and circulates primarily on LDL, but is also present on HDL and Lp(a), increasing proportionally on Lp(a) with higher Lp(a) levels. On average, it has been estimated that only 1 out of 100 LDL particles carry Lp-PLA$_2$. However, on an equimolar basis, Lp(a) has a 1.5-2-fold higher mass of Lp-PLA$_2$ and up to 7-fold higher specific activity than LDL. Lp-PLA$_2$ mass and activity independently predict CVD events and this risk is approximately doubled when Lp(a) and/or OxPL/apoB are also elevated, suggesting a common pathophysiological link. Interestingly, Lp-PLA$_2$ on HDL is associated with lower CVD risk, whereas on LDL it is associated with higher risk. Overall, these observations suggest plausible mechanisms through which Lp(a)-Lp-PLA$_2$-OxPL may mediate CAVS, as has been suggested for atherosclerosis and cardiovascular disease. The disclosure provides antibodies capable of binding OxPL and thus inhibiting their metabolism and effects.

Oxidized phospholipids (OxPL) (phospholipids with a phosphocholine (PC) headgroup) are highly pro-inflammatory and proatherogenic. They are present in a wide spectrum of inflammatory diseases, including atherosclerosis, rheumatoid arthritis (e.g., see FIG. 1), diabetic nephropathy, CNS diseases including multiple sclerosis, and a spectrum of acute and chronic pulmonary diseases. For example, OxPL are present in the lungs of both mice and humans infected with a wide variety of viral and bacterial pathogens (e.g., see FIG. 1). OxPL are abundant in bronchial alveolar lavage (BAL) of mice with these infections as well as in acute respiratory distress syndrome following acid installation, or in BAL of mice with COPD secondary to smoking. OxPL are proinflammatory mediators for macrophages, by inducing IL-6 for example, or alternatively inhibit the capacity of macrophages to phagocytize bacteria. OxPL are prevalent in livers of patients and mice with NASH, and have been shown to be involved in the pathogenesis in murine models of NASH. OxPL are also extensively present in atherosclerotic lesions (e.g., see FIG. 1A), and in vulnerable plaques of human coronary arteries. They are also released into the circulation during interventional procedures such as PCI and stenting, where they likely mediate downstream proinflammatory and vasoactive effects.

Innate natural antibodies (NAbs) provide the first line of host defense against common oxidation-specific epitopes (OSE) on endogenous neo-epitopes (OxLDL and apoptotic cells) and exogenous epitopes of pathogens, and maintain host homeostasis. OSEs are ubiquitous, formed in many inflammatory tissues, including atherosclerotic lesions, and are a major target of IgM NAbs. The prototypic IgM NAb E06, binds to the phosphocholine (PC) headgroup in oxidized phospholipids (OxPL), and blocks uptake of OxLDL by macrophages. We have cloned and characterized a murine IgM natural antibody to OxPL that binds to the phosphorylcholine ("PC") headgroup of OxPL but not to native, non-oxidized phospholipids ("PL").

However, antibodies like IgM Nab E06 have limited solubility and cannot be readily synthesized. Features which are important for generating transgenic animal models.

The parent E06 antibody is a murine IgM antibody that was cloned and characterized and which is the subject of U.S. Pat. No. 6,225,070, which is incorporated herein by reference. This disclosure describes a fully functional single chain antibody and humanized antibodies that bind to OxPL. It describes the numerous unique molecular changes to the DNA sequence of the parent antibody framework regions, heavy and light chains, and a linker sequences that was determined by repeated rounds of experimentation, which resulted in the development of a fully functional E06-scFv. When this sequence is inserted into the appropriate vector, the resultant scFc is expressed in a soluble form, and possesses all the immunological binding properties of the parent toward its identified target antigens, including the ability to bind to a unique anti-idiotypic antibody, AB1-2, whose epitopes consists of both the heavy and light chains of the parent antibody.

The disclosure also provides for single chain variable antibody fragments ("scFv"), $V_H$, $V_L$ and complementarity determining regions that selectively bind to oxidized phospholipids. The scFvs of the disclosure are soluble and can be readily synthesized. Further, vectors comprising sequences encoding the scFvs disclosed herein enabled the production of a transgenic murine model.

Figure 3:
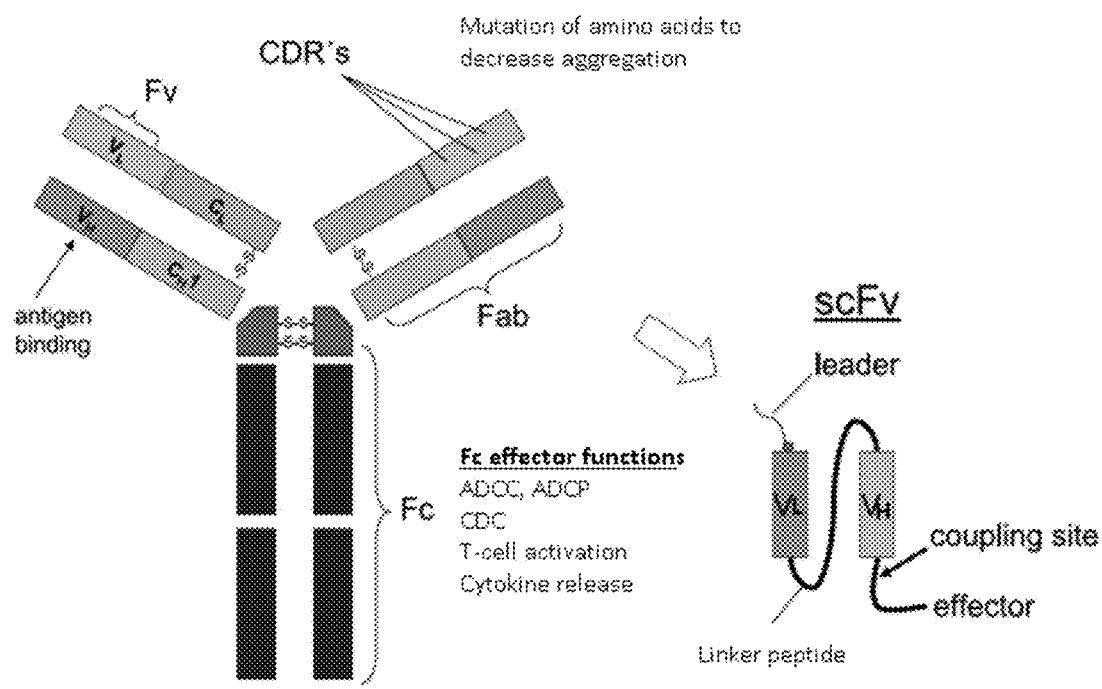
FIG. 3 provides a diagram of the process used to produce single-chain variable fragment ("scFv") of the disclosure. As indicated, site directed mutagenesis was employed to mutate the variable domain of the heavy chain ("V$_H$") of a double chain immunoglobulin antibody to increase the solubility of scFv (left). Linker, leader, and effector regions of the scFv are also indicated (right).

To produce the scFvs of the disclosure, substantial and extensive changes were made in variable heavy chain regions of an OxPL selective IgM antibody, a suitable linker peptide composition and length had to be determined, and a suitable effector and leader sequence had to be generated (e.g., see FIG. 3). Furthermore, a synergy had to be reached with the aforementioned DNA manipulations so as to provide optimal folding of the variable region heavy and light chains to enable the generation of a soluble ScFv that fully retained the biological binding properties of its parent antibody, including the ability to bind to the anti-idiotypic antibody AB1-2 specific for the idiotype of this antibody. The ScFvs disclosed herein therefore provides for therapeutic applications heretofore not possible with double chain antibodies known in the art.

In the development of E06-scFv of the disclosure, attempts to utilize the native framework regions and variable regions of the E06 antibody to generate a scFv did not enable the production of a soluble or functional single chain. Accordingly, to produce the functional and soluble E06-scFv of the disclosure required extensive experimentation based upon trial and error, which included multiple rounds of site directed mutagenesis at multiple sites in the complementary determining ("CDR") regions of the E06 parent antibody, and testing a large number of different linker sequences.

The disclosure provides antibodies, antibody fragments and humanized antibodies that bind to OxPL and which in some instances have the same or similar binding specificity as the E06 antibody. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to tumors, plaques and diseased tissue. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. Coli*, thus allowing the facile production of large amounts of these fragments. Antibody fragments can be isolated from the antibody phage libraries. Alternatively, Fab'-SH fragments can be directly recovered from *E. Coli* and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

The disclosure, although providing specific antibody sequences and antibody sequence fragments having biological activity, further disclose that these sequence can be used to generate improved variants. Accordingly, in some instances an antibody or antibody fragment may have a percent identity to the sequences of the disclosure.

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as Arg, Asp, His, Lys, and Glu) and replaced by a neutral or negatively charged amino acid (e.g., Alanine or Polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody. Polyhistidine tags are also useful for purification.

In certain embodiments, an antibody of the disclosure is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn of the $CH_2$ domain of the Fc region. See, e.g., Wright et al. (1997) TIBTECH 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

For example, antibody variants are provided having a carbohydrate structure that lacks fucose attached (directly or indirectly) to an Fc region. Such variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, an antibody variant comprises an Fc region with one or more amino acid substitutions which further improve ADCC. Such substitutions may occur in combination with any of the variations described above.

In certain embodiments, the disclosure contemplates an antibody variant that possesses some but not all effector functions, which make it a desirable candidate for many applications in which the half-life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks a particular binding but retains other binding. Non-limiting examples of in vitro assays to assess ADCC activity of a molecule of interest is described in U.S. Pat. No. 5,500,362 (see, e.g. Hellstrom, I., et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assays methods may be employed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). Clq binding assays may also be carried out to confirm that the antibody is unable to bind Clq and hence lacks CDC activity. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, for example, Petkova, S. B. et al., Int'l. Immunol. 18(12):1759-1769 (2006)).

Other antibody variants having one or more amino acid substitutions are provided. Sites of interest for substitutional mutagenesis include the hypervariable regions, but FR alterations are also contemplated. Conservative substitutions can also be performed. Amino acid substitutions may be introduced into an antibody of interest and the products screened, e.g., for a desired activity, such as improved antigen binding, decreased immunogenicity, improved ADCC or CDC, etc.

The disclosure provides an antibody or antibody fragment capable of binding to OxPL or phosphorylcholine and/or a phosphorylcholine conjugate, wherein the antibody or antibody fragment comprises a variable heavy chain ($V_H$) domain and/or a variable light chain ($V_L$) domain, and wherein (a) the $V_H$ domain comprises an amino acid sequence that includes one, two or three complementarity determining regions (CDRs) selected from the group consisting of:
  (i) SEQ ID NO:6 and sequence that are at least 95%, 96%, 97%, 98%, 99% or 99.9% identical to SEQ ID NO:6;
  (ii) SEQ ID NO:7 and sequence that are at least 95%, 96%, 97%, 98%, 99% or 99.9% identical to SEQ ID NO:7; and
  (iii) SEQ ID NO:8 and sequence that are at least 95%, 96%, 97%, 98%, 99% or 99.9% identical to SEQ ID NO:8; (b) the $V_L$ domain comprises an amino acid sequence that includes one, two or three complementarity determining regions (CDRs) selected from the group consisting of:
  (i) SEQ ID NO:9 or 12 and sequence that are at least 95%, 96%, 97%, 98%, 99% or 99.9% identical to SEQ ID NO:9 or 12;
  (ii) SEQ ID NO:10 and sequence that are at least 95%, 96%, 97%, 98%, 99% or 99.9% identical to SEQ ID NO:10; and
  (iii) SEQ ID NO:11 and sequence that are at least 95%, 96%, 97%, 98%, 99% or 99.9% identical to SEQ ID NO:11.

In one embodiment, the antibody or antibody fragment comprises a $V_H$ domain that comprises an amino acid sequence that includes CDRs comprising SEQ ID NO:6, 7 and 8, and/or the $V_L$ domain comprises an amino acid sequence that includes CDRs comprising SEQ ID NO:9, 10 and 11, or SEQ ID NO:10, 11 and 12.

In one embodiment, the disclosure provides an antibody or an scFv selected from the group consisting of: (a) an antibody or scFv with heavy and light chain domains comprising the complementarity determining regions of SEQ ID NO:6, 7, 8, 9, 10 and 11; and (b) an antibody or scFv with heavy and light chain domains comprising the complementarity determining regions of SEQ ID NO:6, 7, 8, 10, 11 and 12. In one embodiment either of (a) or (b) are linked to an Fc region.

In one embodiment, the disclosure provides an antibody comprising a light-chain variable region as set forth in SEQ ID NO:2 from amino acid 1 to about 146. In another embodiment, the disclosure provides an antibody with a humanized light chain variable region comprising the sequence of SEQ ID NO:4 from amino acid 1 to about 135. In another embodiment, the disclosure provides an antibody that comprises a heavy chain variable region comprising a sequence of SEQ ID NO:2 from about 162 to about 269. In another embodiment, the disclosure provides an antibody that comprises a humanized heavy chain variable region comprising a sequence of SEQ ID NO:4 from about 152 to about 258.

In another embodiment, the disclosure provides a chimeric antibody comprising, for example, a murine VH and/or VL and a human Fc region. For example, SEQ ID NO:14 provides the sequence of a chimeric antibody of the disclosure. In SEQ ID NO:14 amino acids 1-33 comprise and Ig kappa chain leader sequence for antibody secretion; amino acid 34-146 comprise an E06 light-chain variable region; amion acids 147-161 provide a flexible linker sequence; amino acids 162-284 provide an E06 heavy-chain variable region with a triple mutation of P201A, S224A and A225D relative to the wild-type urine E06 antibody; amino acids 285-517 comprise an Fc region, in SEQ ID NO:14 the Fc region is a human IgG1-Fc with a modification of C290S and H294Y to increase ADCC activity. SEQ ID NO:14 also provide a further linker and His tag sequence, which one of skill in the art are optional (e.g., SEQ ID NO:14 from amino acid 518 to 528). The disclosure also contemplates and provides a coding sequence for SEQ ID NO:14 comprising SEQ ID NO:13. One of skill in the art can readily identify the nucleic acid sequence corresponding to the various domains identified above. The disclosure also includes a chimeric antibody sequence that is at least 90%, 95%, 96%, 97%, 98%, 99% or 99.9% identical to SEQ ID NO:14 from amino acid 1 to 284 linked to an Fc region from an different immunoglobulin (e.g., IgA, IgD, IgE, IgG, and IgM, or any of the subclasses (isotypes), e.g., $IgG_1$, $IgG_2$, $IgG_3$, $IgG_4$, $IgA_1$, and $IgA_2$).

In one embodiment, the disclosure provides an scFv comprising a linker between the light change variable region and the heavy-chain variable region. The linker can be any number of commonly used peptide linkers. In one embodiment, the linker comprises a repeating unit of GGGS (SEQ ID NO:5). The repeat of GGGS (SEQ ID NO:5) may be 2, 3, 4 or more times.

In another embodiment, the disclosure comprises a scFv comprising a light chain variable region of SEQ ID NO:2 from amino acid 1 to 146 linked by a peptide linker to a heavy chain variable region of SEQ ID NO:2 from amino acid 162 to about 269. In a specific embodiment, the scFv comprises a sequence of SEQ ID NO:2 form amino acid 1 to 269. In another embodiment, the disclosure provides for an scFv which has a polypeptide sequence of SEQ ID NO:2 from amino acid 1 to about 269 or 1 to about 303. In a further embodiment, the disclosure provides for an scFv that has a polypeptide sequence that has at least 75%, at least 80%, at least 85%, at least 90%, at least 95%, at least 98%, or at least 99% sequence identity to SEQ ID NO:2 from amino acid 1 to about 303 and which selectively binds to an oxidized phospholipid.

In yet further embodiments, fusion constructs comprising a first domain comprising SEQ ID NO:2 from amino acid 1 to about 269 or 1 to about 303 or a variant thereof is operably linked to a second domain comprising (i) a detectable label or (ii) a polypeptide of interest. One of skill in the art will recognize that such fusion constructs can be generated using chemical or molecular biology techniques that link a coding sequence comprising a sequence of SEQ ID NO:1 or variant thereof with a coding sequence of, for example, a polypeptide of interest. The coding sequences and domains may be separated by a linker or directly linked.

In yet another embodiment, the disclosure comprises a scFv comprising a light chain variable region of SEQ ID NO:4 from amino acid 1 to 135 linked by a peptide linker to a heavy chain variable region of SEQ ID NO:4 from amino acid 152 to about 258. In a specific embodiment, the scFv comprises a sequence of SEQ ID NO:4 form amino acid 1 to 258. In another embodiment, the disclosure provides for an scFv which has a polypeptide sequence of SEQ ID NO:4 from amino acid 1 to about 258 or 1 to about 263. In a further embodiment, the disclosure provides for an scFv that has a polypeptide sequence that has at least 75%, at least 80%, at least 85%, at least 90%, at least 95%, at least 98%, or at least 99% sequence identity to SEQ ID NO:4 from amino acid 1 to about 258 and which selectively binds to an oxidized phospholipid.

In yet further embodiments, fusion constructs comprising a first domain comprising SEQ ID NO:4 from amino acid 1 to about 258 or 1 to about 264 or a variant thereof is operably linked to a second domain comprising (i) a detectable label or (ii) a polypeptide of interest. One of skill in the art will recognize that such fusion constructs can be generated using chemical or molecular biology techniques that link a coding sequence comprising a sequence of SEQ ID NO:3 or variant thereof with a coding sequence of, for example, a polypeptide of interest. The coding sequences and domains may be separated by a linker or directly linked.

Nucleic acid molecules encoding the amino acid sequences of the antibodies, antibody fragments and variants of the antibody are prepared by a variety of methods known in the art. For preparing variants such methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

In a particular embodiment, the disclosure provides for a murine scFv which is encoded by a polynucleotide sequence of SEQ ID NO:1. In a further embodiment, the disclosure provides for a murine scFv which is encoded by a polynucleotide sequence that has at least 75%, at least 80%, at least 85%, at least 90%, at least 95%, at least 98%, or at least 99% sequence identity to SEQ ID NO:1 and which produces a polypeptide that selectively binds to oxidized phospholipids.

The disclosure also encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies. See, e.g., Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

In a particular embodiment, the disclosure provides for a humanized scFv which is encoded by a polynucleotide sequence of SEQ ID NO:3. In a further embodiment, the disclosure provides for a humanized scFv which is encoded by a polynucleotide sequence that has at least 75%, at least 80%, at least 85%, at least 90%, at least 95%, at least 98%, or at least 99% sequence identity to SEQ ID NO:3 and which produces a polypeptide that selectively binds to oxidized phospholipids.

The disclosure further provides for a scFv disclosed herein that further comprises a fragment crystallizable region ("Fc") of an antibody. In a particular embodiment, the Fc region is from a human or humanized antibody. The Fc region is the tail region of an antibody that interacts with cell surface receptors called Fc receptors and some proteins of the complement system. This property allows antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains ($C_H$ domains 2-4) in each polypeptide chain. The Fc regions of IgGs bear a highly conserved N-glycosylation site. Glycosylation of the Fc fragment is essential for Fc receptor-mediated activity. The N-glycans attached to this site are predominantly core-fucosylated diantennary structures of the complex type. In addition, small amounts of these N-glycans also bear bisecting GlcNAc and α-2,6 linked sialic acid residues. The other part of an antibody, called the Fab region, contains variable sections that define the specific target that the antibody can bind. The scFv of the disclosure are comprised of elements from the Fab region. By contrast, the Fc region of all antibodies in a class are the same for each species; they are constant rather than variable. The Fc region is, therefore, sometimes termed the "fragment constant region". Accordingly, the polynucleotide and polypeptide sequences which encode the Fc regions for countless species have already been determined and would be known by one of skill in the art. In a particular, embodiment, the disclosure provides for an scFv polynucleotide sequence disclosed herein (i.e., SEQ ID NO:1) that further comprises a polynucleotide sequence which encodes an Fc region from IgG antibody (e.g., from a human IgG antibody). In a further embodiment, the disclosure provides for an scFv polypeptide sequence disclosed herein (i.e., SEQ ID NO:2 from amino acid 1 to about 303) that further comprises a polypeptide sequence of an Fc region from an IgG antibody.

In a particular, embodiment, the disclosure provides for a scFv polynucleotide sequence disclosed herein (i.e., SEQ ID NO:3 from 1 to about 789) that further comprises a polynucleotide sequence which encodes an Fc region from IgG antibody (e.g., from a human IgG antibody). In a further embodiment, the disclosure provides for an scFv polypeptide sequence disclosed herein (i.e., SEQ ID NO:4 from amino acid 1 to about 258 or about 1 to 263) that further comprises a polypeptide sequence of an Fc region from an IgG antibody (e.g., SEQ ID NO:4 from about amino acid 264 to about 506. In one embodiment the coding sequence for the Fc region comprises a sequence as set forth in SEQ ID NO:3 from about nucleotide 790 to about nucleotide 1518.

In a further embodiment, the disclosure provides for a vector which comprises a polynucleotide sequence encoding a scFv as set forth above with reference to SEQ ID NO:1 and 3 or sequences having sequence identity of at least 99%, at least 95%, at least 90%, at least 85%, at least 80%, at least 75% or at least 70% identity to SEQ ID NO:1 or SEQ ID NO:3 and which encodes a polypeptide that specifically binds to an oxidized phospholipid.

The disclosure also provides a humanized antibody that has the binding specificity of an E06 antibody. The humanized antibody comprises (i) a sequence as set forth in SEQ ID NO:4 from amino acid 1 to about amino acid 506 or (ii) a sequence that is at least 90%, 91%, 92%, 93%, 94%, 95%, 96%, 97%, 98%, 99%, 99.5% or 99.8% identical to SEQ ID NO:4 from amino acid 1 to about 506.

The disclosure also provide a polynucleotide that encodes a humanized antibody of the disclosure. The polynucleotide comprises a sequence selected from the group consisting of (i) a polynucleotide that encodes SEQ ID NO:4, (ii) a polynucleotide that hybridizes under stringent conditions to a polynucleotide consisting of SEQ ID NO:3 and encodes a humanized antibody that binds to OxPL with a specificity substantially similar to the E06 antibody, (iii) a polynucleotide that is at least 90%, 91%, 92%, 93%, 94%, 95%, 96%, 97%, 98%, 99%, 99.5% or 99.8% identical to SEQ ID NO:3 and which encodes an antibody that binds to OxPL with a specificity substantially similar to the E06 antibody; (iv) a polynucleotide as set forth in SEQ ID NO:3 and (v) a polynucleotide of any of (i) to (iv) wherein the polynucleotide comprises RNA.

Figure 22:
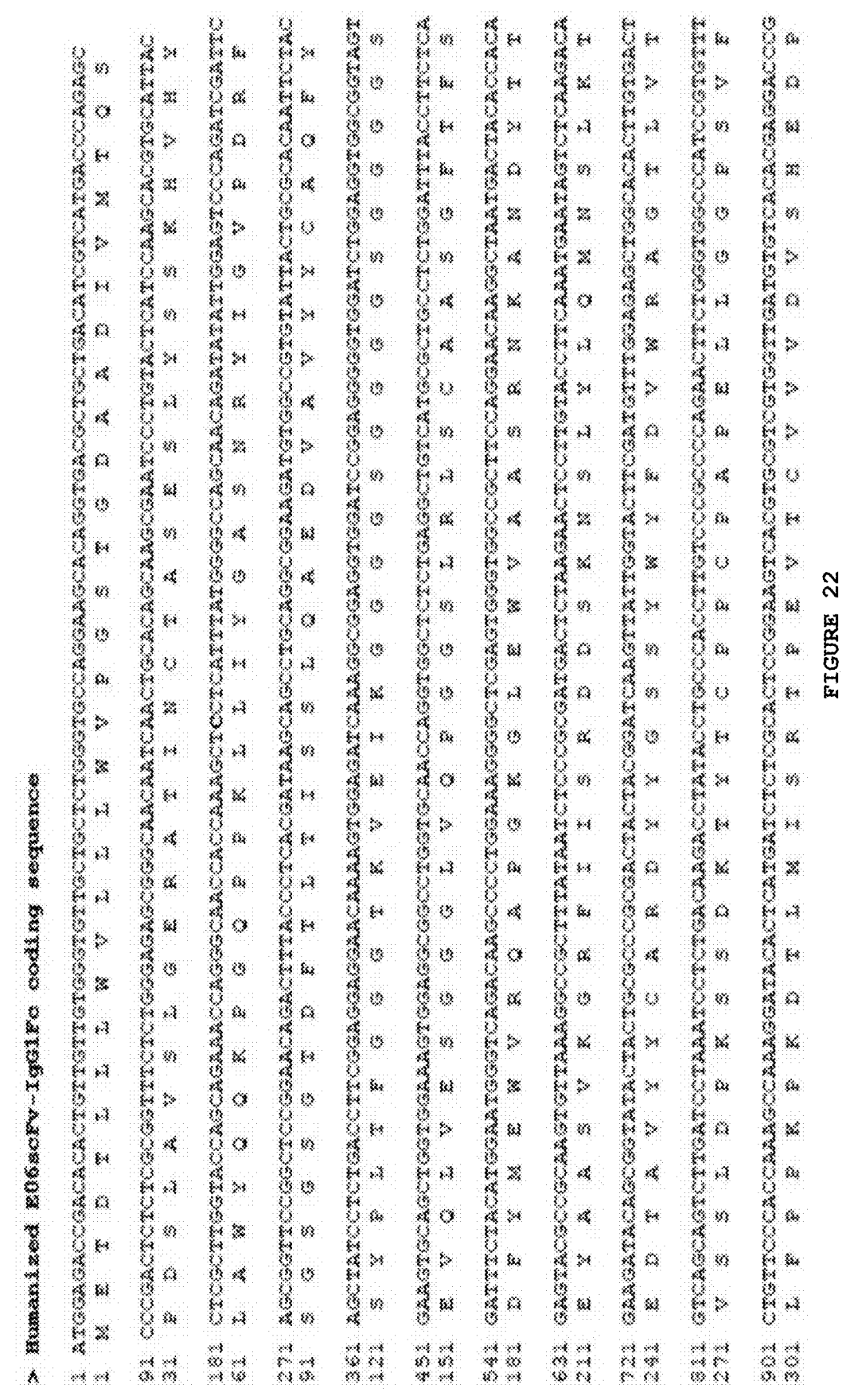
Figure 22:
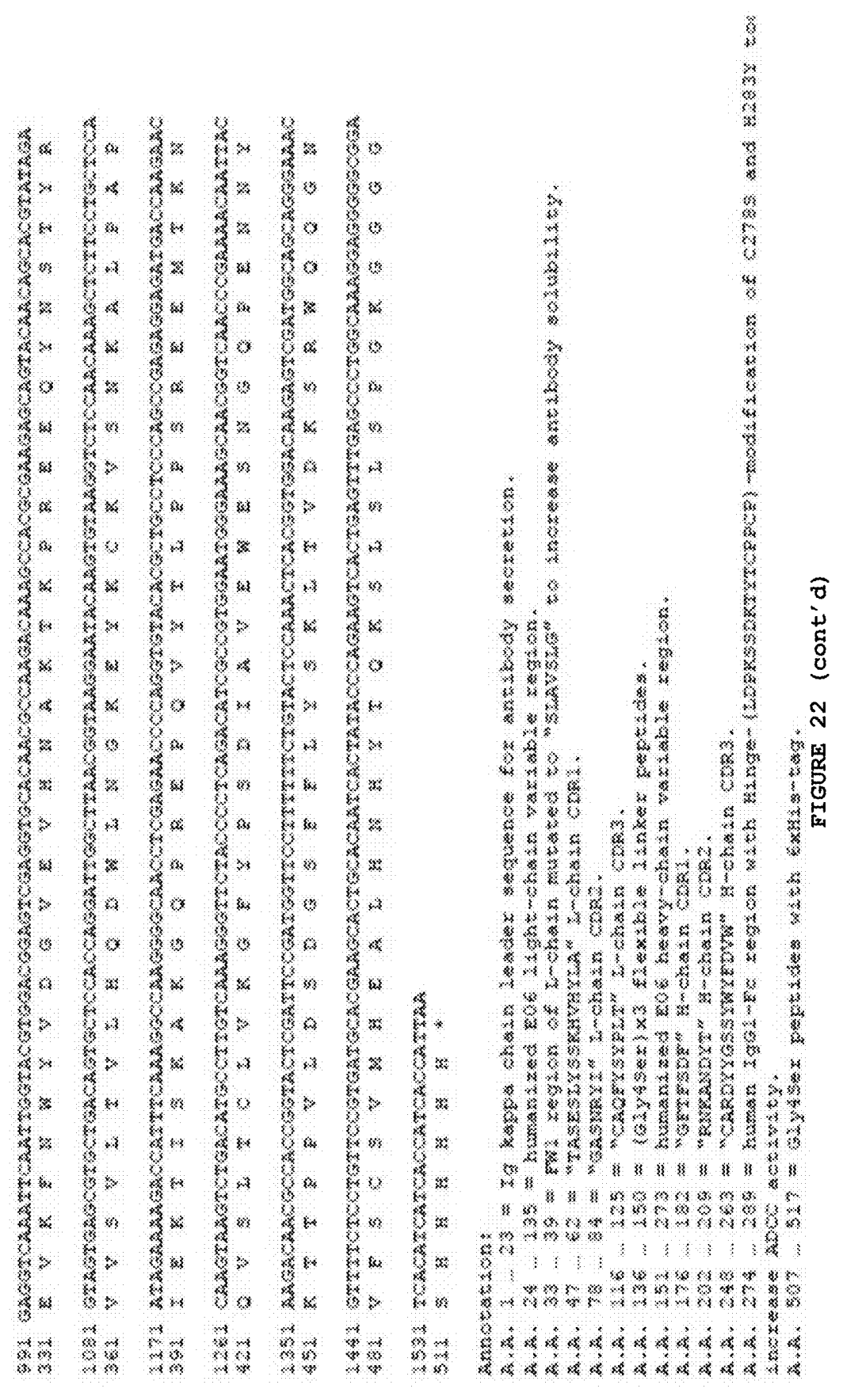

FIGS. 20, 21 and 22 provide sequences of the disclosure. One of skill in the art can readily recognize the coding sequences for various "domain" of the antibodies and antibody fragments with reference to FIGS. 20, 21 and 22. The disclosure contemplates the use of sequences corresponding to various domains, particularly CDR domains from the sequences set forth below. The CDRs can be shuffled into antibody frameworks to provide novel antibodies that have recognition domains for oxidized phospholipids.

Polynucleotide sequences encoding polypeptide components of the antibody or antibody fragments of the disclosure can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. Coli is typically transformed using pBR322, a plasmid derived from an E. Coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage vectors may be utilized in making a recombinant vector which can be used to transform susceptible host cells such as E. Coli LE392.

The expression vector of the disclosure may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the (3-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one embodiment, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another embodiment, the production of the immunoglobulins according to the disclosure can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. Coli* trxB-strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the invention include Archaebacteria and Eubacteria, such as Gram-negative or Gram-positive organisms. Examples of useful bacteria include *Escherichia* (e.g., *E. Coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In one embodiment, gram-negative cells are used. In one embodiment, *E. Coli* cells are used as hosts for the disclosure. Examples of *E. Coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 (U.S. Pat. No. 5,639,635). Other strains and derivatives thereof, such as *E. Coli* 294 (ATCC 31,446), *E. Coli* B, E. ColiX 1776 (ATCC 31,537) and *E. Coli* RV308 are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. Coli, Serratia*, or *Salmonella* species can be suitably used as the host when well-known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the disclosure are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures.

In one embodiment, the expressed polypeptides are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Large scale or small scale fermentation can be used and can be optimized using skills well known in the art.

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration.

Figure 4:
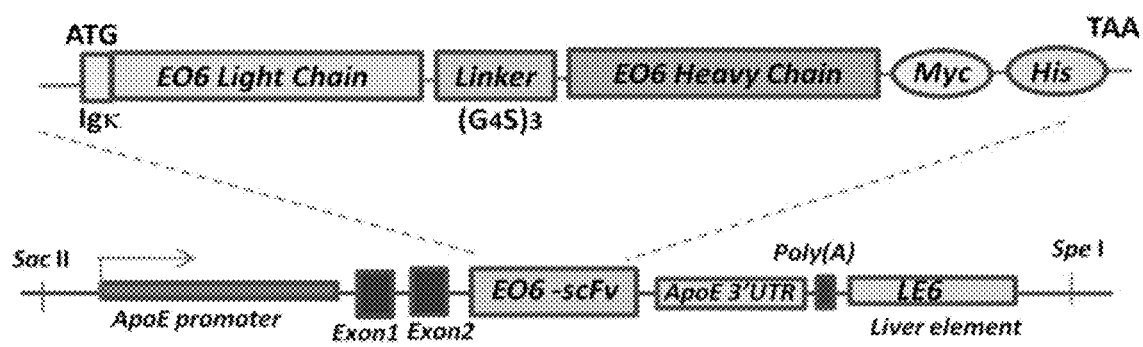
FIG. 4 provides a generalized map demonstrating the layout of the genetic components that encode the scFv E06 antibody fragment (top); and a generalized vector map indicating the encoding sequence for the E06-scFv antibody fragment in relation to other vector elements that was used to generate transgenic mice (bottom).

The disclosure further provides for an expression vector which can be replicated in a prokaryotic system or a eukaryotic system, the vector comprising at least one polynucleotide encoding a scFv disclosed herein or a coding sequence for a humanized antibody (e.g., see FIG. 4). In one embodiment, the disclosure provides for an expression vector which comprises a polynucleotide sequence encoding a scFv having sequence identity of at least 100%, at least 99%, at least 95%, at least 90%, at least 85%, at least 80%, at least 75% or at least 70% identity to SEQ ID NO:1 or SEQ ID NO:3. In a further embodiment, when a sequence encoding a scFv disclosed herein (i.e., a polynucleotide have 90% or more sequence identity to SEQ ID NO:1 or 3) is inserted into the appropriate vector, the resultant scFv or humanized antibody is expressed in a soluble form, and possesses all the immunological binding properties of the E06 antibody toward its identified target antigens, including the ability to bind to a unique anti-idiotypic antibody, AB1-2, whose epitopes comprise both the heavy and light chains of the parent antibody. In yet a further embodiment, the resultant scFv or humanized antibody that is expressed has a sequence identity of at least 100%, at least 99%, at least 95%, at least 90%, at least 85%, at least 80%, at least 75% or at least 70% identity to SEQ ID NO:2 or 4, wherein the polypeptide is expressed in a soluble form, and possesses all the immunological binding properties of the E06 antibody toward its identified target antigens.

The disclosure further provides for an expression vector which encodes a scFv or humanized antibody disclosed herein that is transferred into a suitable host organism. The suitable host organism is a microorganism, yeast or a mammalian cell system. Typically, the mammalian cell system is monocyte-derived (e.g., macrophages, monocytes, and neutrophils), lymphocyte-derived (e.g., myeloma, hybridoma, and a normal immortalized B cell), parenchymal (e.g., hepatocytes) and non-parenchymal cells (e.g., stellate cells).

The scFv disclosed herein (humanized or non-humanized) or a scFv disclosed herein which further comprises an IgG Fc region (e.g., IgG equivalent), e.g., a humanized antibody comprising SEQ ID NO:4, can be used for many possible therapeutic uses. For example, they can be used as an anti-inflammatory agent, and/or as an anti-atherosclerotic agent. As an anti-inflammatory agent, a scFv (humanized or non-humanized) of the disclosure or a humanized antibody of the disclosure can be used to treat acute respiratory distress, acute fulminating pneumonias, or other similar disorders. Moreover in studies presented herein, E06-scFv was found to inhibit an immunologically induced arthritis model and therefore a scFv (humanized or non-humanized) of the disclosure or a humanized antibody of the disclosure would be of great benefit for treating inflammatory-related conditions with or without immunological suppression. The scFv (humanized or non-humanized) of the disclosure or a humanized antibody of the disclosure can also be used be used to treat patients with acute hepatitis, or with NASH and metabolic syndrome. Furthermore, a scFv (humanized or non-humanized) of the disclosure or a humanized antibody of the disclosure can be used to treat any condition, disorder, or disease where OxPL plays a causative role in generating an abnormal state. Additionally, E06-scFv can bind to the PC present on the cell wall of *S. pneumonia* (and other pathogens) and therefore a scFv (humanized or non-humanized) of the disclosure or a humanized antibody of the disclosure can provide in vivo protection to a subject against lethal or severe pneumococcal disease.

The disclosure also provides that a scFv (humanized or non-humanized) of the disclosure or a humanized antibody of the disclosure can be used as an anti-atherosclerotic agent to treat cardiovascular disease and CAS. Moreover, material trapped in distal protection devices following percutaneous coronary intervention ("PCI") procedures on human coronary lesions during interventional procedures and using immunological and mass spectrometry techniques, showed an abundant OxPL release. A coinjection of a scFv (humanized or non-humanized) of the disclosure or a humanized antibody of the disclosure could effectively bind and block downstream proinflammatory or vasoactive effects and/or treat patients with acute coronary syndromes or with "crescendo angina." A scFv (humanized or non-humanized) of the disclosure or a humanized antibody of the disclosure can be used as a proactive measure in treating high risk patients, e.g. patients who have a propensity for stroke or developing atherosclerosis. It should be noted that a scFv (humanized or non-humanized) of the disclosure or a humanized antibody of the disclosure can lower inflammation systemically in mice. Accordingly, it can be expected that a scFv (humanized or non-humanized) of the disclosure or a humanized antibody of the disclosure can be used to treat high risk patients with coronary artery disease ("CAD"), by inhibiting of IL-lb expression and/or signaling.

The disclosure also provides a method of treating patients with a scFv (humanized or non-humanized) of the disclosure or a humanized antibody of the disclosure or other small molecules presenting with aortic stenosis to prevent progression and obviate the need for surgical replacement and all of the risk involved with such invasive options, either acutely during the operation or later with anticoagulation therapy that is needed and possibly repeat surgery. The antibody or small molecule has the potential for inhibiting the effects of oxidized phospholipids on the aortic valve to prevent or treat calcific aortic stenosis. Since E06 can be expressed by macrophages suggests that the possibility of a strategy to provide sustained systemic levels of a scFv (humanized or non-humanized) of the disclosure or a humanized antibody of the disclosure in patients.

Additionally, the disclosure also provides for a unique transgenic animal model that expresses a scFv disclosed herein from both the liver and from macrophages. This animal model allows for a systematic study of the therapeutic effects of the scFvs of the disclosure in a wide variety of physiological and pathophysiological settings. It should also be understood that while the studies presented herein were conducted with a transgenic murine model that the methods and compositions presented herein can be equally as well be applied to create transgenic models in any number of animals including, but not limited to, rats, rabbits, pigs, sheep, goats, and horses. The disclosure, therefore, provides methods which can be performed in vivo to study the therapeutic possibilities of a scFv (humanized or non-humanized) of the disclosure or a humanized antibody of the disclosure in a highly defined manner. For example, a desirable scFv can be produced during cell culturing or in a transgenic animal. The availability of a transgenic animal model expressing a scFv disclosed herein allows for in-depth preclinical testing for myriad of potential applications. For example, interventions can be done on the transgenic animals to test the impact of scFv expression, including, by breeding the animals into a variety of backgrounds. Additionally, because macrophages are able to express the scFv of the disclosure, bone marrow transplantation from the transgenic animal to a wide variety of other animal models may be sufficient to test the impact of expressing scFvs disclosed herein in a variety of settings, without the need to do extensive breeding. As the disclosure further provides for a scFv sequence disclosed herein which further comprises an Fc region from an IgG antibody (i.e., an IgG equivalent) this will allow for a comparison of the effects of an "intact" IgG vs. those of the scFv alone, which effects are an important consideration for administering a scFv disclosed herein for human use. Accordingly, the scFv disclosed herein have great potential for use in clinical applications. Moreover, the availability of transgenic animals expressing a fully functional scFv (or an IgG equivalent) provides a highly efficient path for preclinical testing and clinical applications.

The scFvs disclosed herein bind to OxPLs and block their pro-inflammatory effects. It is anticipated that the in vivo use of a scFv (humanized or non-humanized) of the disclosure or a humanized antibody of the disclosure can be used to blockade OxPL biological effects in many different situations. For example, it has been shown that OxPLs are released from atherosclerotic coronary arteries when these arteries are undergoing surgical procedures to implant and/or expand stents. These released OxPLs could bring about adverse vasoactive effects throughout the patient's body. Acute and/or chronic injection/infusion of a scFv (humanized or non-humanized) of the disclosure or a humanized antibody of the disclosure therefore could block these adverse effects and/or alternatively block or attenuate similar ischemic events, such as acute coronary syndromes or acute strokes. Similarly, a scFv (humanized or non-humanized) of the disclosure or a humanized antibody of the disclosure could also be infused to a subject so as to block proinflammatory effects mediated by OxPLs generated from a variety of pathological conditions, such as respiratory distress secondary to chemical, viral or bacterial infection, or in acute exacerbations of chronic obstructive pulmonary disease ("COPD") where OxPLs have been shown to impair macrophage clearance of bacterial infections. Accordingly, a scFv (humanized or non-humanized) of the disclosure or a humanized antibody of the disclosure would be effective anti-inflammatory agents in other systemic inflammatory settings such as in rheumatoid arthritis, or by inhibiting the inflammatory events associated with NASH and NAFLD. Accordingly, a scFv (humanized or non-humanized) of the disclosure or a humanized antibody of the disclosure can be used in many clinical applications or settings where anti-inflammatories and/or anti-atherosclerotic agents need to be administered temporally and/or chronically. Further, by the fact that E06-scFv was expressed from macrophages provides for the use of a scFv (humanized or non-humanized) of the disclosure or a humanized antibody of the disclosure in strategies to provide sustained systemic expressed levels of a scFv (humanized or non-humanized) of the disclosure or a humanized antibody of the disclosure in humans.

Thus, the antibodies, antibody fragments and polypeptides of the disclosure can be used to treat inflammatory diseases and disorders, cardiovascular diseases, and diseases associated with oxidized phospholipids. The term cardiovascular diseases, is intended to include but is not limited to atherosclerosis, acute coronary syndrome, acute myocardial infarction, myocardial infarction (heart attack), stable and unstable angina pectoris, aneurysms, coronary artery disease (CAD), ischemic heart disease, ischemic myocardium, cardiac and sudden cardiac death, cardiomyopathy, congestive heart failure, heart failure, stenosis, peripheral arterial disease (PAD), intermittent claudication, critical limb ischemia, and stroke.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, a scFv (humanized or non-humanized) of the disclosure or a humanized antibody of the disclosure are used to delay development of a disease or disorder.

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

An "effective amount" refers to an amount effective, at dosages and for periods of time necessary, to achieve the desired therapeutic or prophylactic result.

A "therapeutically effective amount" of a substance/molecule of the disclosure, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

Therapeutic formulations comprising an antibody or fragment thereof of the disclosure are prepared for storage by mixing the antibody or fragment having the desired degree of purity with optional physiologically acceptable carriers, excipients or stabilizers (Remington: The Science and Practice of Pharmacy 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and yethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Anti-OxPL antibodies of the disclosure can be produced transgenically through the generation of a mammal or plant that is transgenic for the immunoglobulin heavy and light chain sequences of interest and production of the antibody in a recoverable form therefrom. In connection with the transgenic production in mammals, anti-OxPL antibodies can be produced in, and recovered from, the milk of goats, cows, or other mammals. See, e.g., U.S. Pat. Nos. 5,827,690, 5,756,687, 5,750,172, and 5,741,957, incorporated herein by reference.

In some embodiments, non-human transgenic animals or plants are produced by introducing one or more nucleic acid molecules encoding an anti-OxPL antibody or fragment thereof (e.g., SEQ ID NO:1, 3 or 13) of the disclosure into the animal or plant by standard transgenic techniques. See Hogan and U.S. Pat. No. 6,417,429. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al., Manipulating the Mouse Embryo: A Laboratory Manual 2.sup.nd ed., Cold Spring Harbor Press (1999); Jackson et al., Mouse Genetics and Transgenics: A Practical Approach, Oxford University Press (2000); and Pinkert, Transgenic Animal Technology: A Laboratory Handbook, Academic Press (1999), all incorporated herein by reference. In some embodiments, the transgenic non-human animals have a targeted disruption and replacement by a targeting construct that encodes a heavy chain and/or a light chain of interest. In another embodiment, the transgenic animals comprise and express nucleic acid molecules encoding heavy and light chains that specifically bind to epitopes on OxPL. In some embodiments, the transgenic animals comprise nucleic acid molecules encoding a modified antibody such as a single-chain antibody, a chimeric antibody or a humanized antibody. The anti-OxPL antibodies may be made in any transgenic animal. In another embodiment, the non-human animals are mice, rats, sheep, pigs, goats, cattle or horses. The non-human transgenic animal expresses said encoded polypeptides in blood, milk, urine, saliva, tears, mucus and other bodily fluids.

The following examples are intended to illustrate but not limit the disclosure. While they are typical of those that might be used, other procedures known to those skilled in the art may alternatively be used.

EXAMPLES

Producing and Cloning E06-scFv into a Mammalian Expression Vector.

To produce the functional and soluble E06-scFv of the disclosure required extensive experimentation based upon trial and error, which included multiple rounds of site directed mutagenesis at multiple sites in the CDR regions of the E06 parent antibody, and testing a large number of different linker sequences. A generalized diagram of the process used to produce E06-scFv is provided in FIG. 3, while a map demonstrating genetic components of E06-scFv is provided in FIG. 4, top). The polynucleotide sequence of E06-scFv is provided as SEQ ID NO:1, and polypeptide sequence encoding E06-scFv is provided as SEQ ID NO:2 from amino acid 1 to about 303.

Developing and Testing Transgenic E06-scFv Mice in a Murine Model.

To determine the impact in vivo of sustained titers of E06, we generated transgenic mice expressing a single-chain antibody fragment (scFv) of E06. The E06-scFv was expressed in vivo, using the apoE promoter (see FIG. 4, bottom) and was used to generate transgenic mice ("Tg") in a LdL receptor negative ("Ldlr$^{-/-}$") background.

Figure 5:
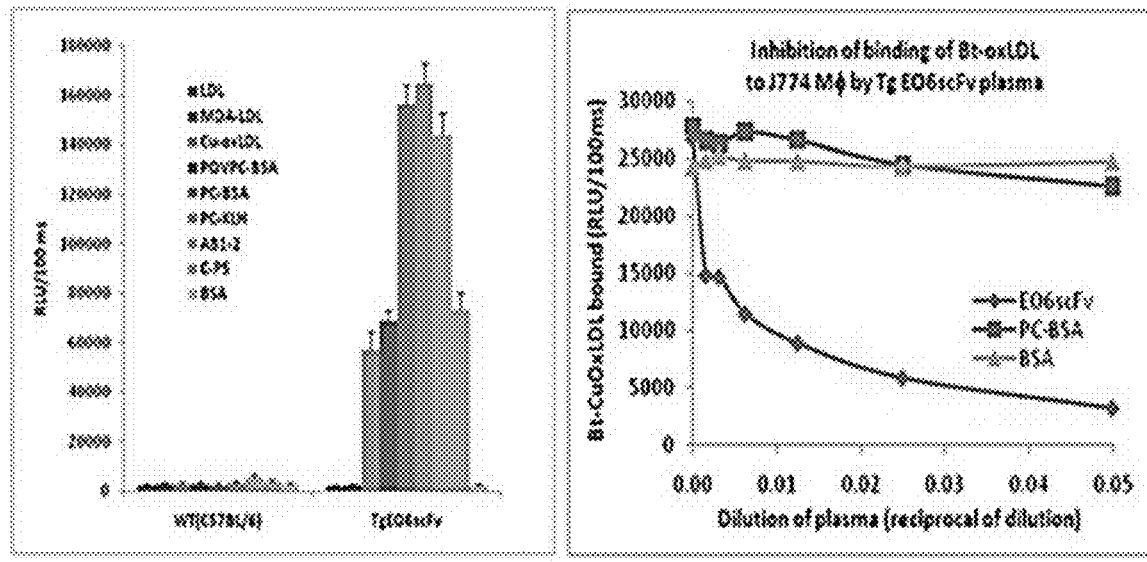
FIG. 5 provides the binding profiles of plasma (1:20) from wild-type C57BL/6 and E06-scFv transgenic mice. The bar graph (left panel) demonstrates the ability of scFv E06 antibody fragment to bind to target antigens, the phosphorylcholine ("PC") of oxidized phospholipid as well as PC on bovine serum albumin ("BSA"). The anti-idiotype antibody AB1-2, which requires both the heavy chain and light chain of the variable regions for its epitope, was bound by E06-scFv antibody fragment. Therefore, the E06-scFv replicate the paratope of the parent antibody. The curves (right panel) show that high dilutions of plasma from transgenic ("Tg") mice still have sufficient Ab titer to block the binding of OxLDL to macrophages. This is a primary mechanism by which the E06-scFv inhibits atherosclerosis. A second mechanism is by blocking proinflammatory effects of oxidized phospholipids. Results reflect a mean of 5 mice from each group by Elisa using anti-myc AP conjugate and Lumi-Phos substrate. AB1-2, anti-T15/E06 idiotypic antibody; C-PS, Capsular polysaccharide of S. pneumonia.

E06-scFv bound to the PC moiety present on the cell wall of many pathogens, such as *S. pneumonia* (see FIG. 5, left). E06-scFv was secreted into the plasma, bound to PC-BSA and OxLDL, and achieved sufficient plasma levels to inhibit binding of OxLDL to macrophages in culture at high plasma dilution (see FIG. 5, right).

Figure 6A:
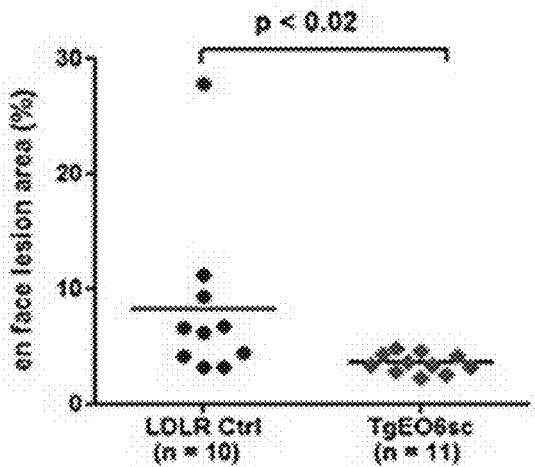
FIG. 6A-B demonstrates that transgenic mice expressing E06-scFv inhibited atherosclerosis in cholesterol-fed LDL-receptor negative ("LDLR") mice. (A) Shows the extent of atherosclerosis in the entire aorta area expressed as a percentage. (B) Shows the extent of lesion at the level of the aortic valve. Atherosclerosis begins in mice at the aortic valve. Shown here is the extent of lesion at different sites starting from the first leaflet of the aortic valve on left and lesions at successive intervals going up the aortic root. In both cases the lesions are significantly smaller in transgenic mice.
Figure 6B:
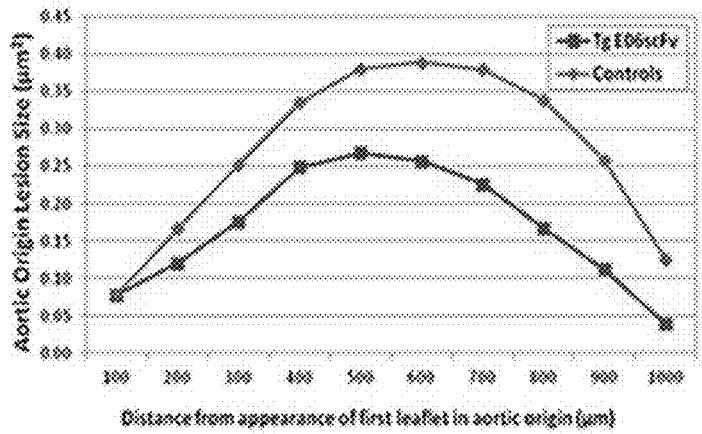

Feeding LDLr$^{-/-}$ mice a high cholesterol diet induces atherosclerosis and also generalized inflammation as indicated by elevated plasma SAA. The extent of atherosclerosis in male Ldlr$^{-/-}$ and Tg Ldlr$^{-/-}$ mice fed 1% cholesterol diet for 16 weeks (n=10-12) was evaluated. While the plasma cholesterol levels were similar, in the Tg mice, en face lesion area was decreased 57% (8.28% vs 3.54%, p<0.02) and lesion area at aortic root decreased 55% (see FIG. 6). Peritoneal macrophages from the E06-scFv-Tg mice had 49% less cholesterol, consistent with decreased OxLDL uptake, and also had decreased inflammatory gene expression. Plasma serum amyloid A ("SAA") was also reduced 32%, consistent with generalized decreased inflammation (see FIG. 6).

In summary, the presence of the E06-scFv reduced the extent of atherosclerosis by 55% over a 16 week time period and dramatically reduced plasma SAA.

The development of the transgenic murine model has facilitated preclinical testing of E06-scFv on an acute or chronic disease processes. The transgenic mice can be subjected to any given inflammatory event, for example, by provoking acute respiratory distress by bronchial installation of offending agent (e.g., acid) and comparing the response between transgenic mice versus a control. The impact of the E06-scFv can be tested in more chronic settings by breeding the transgenic mouse into an appropriate experimental murine model. For example, E06-scFv transgenic mice were bred in the Ldlr$^{-/-}$ background, whereby the mice develop atherosclerosis when fed a high cholesterol diet. In addition, because E06-scFv is synthesized and secreted by macrophages as well, one could transfer bone marrow from E06-scFv transgenic mice into a recipient, and evaluate the expression of the antibody on a biological process in those mice, without the need for extensive breeding. As noted above this allows direct study of the impact of the scFv on disease endpoints and also provides murine models to allow study of the mechanisms by which the antibody achieves its biological effects.

Bone Marrow Transplantation Studies.

Figure 7:
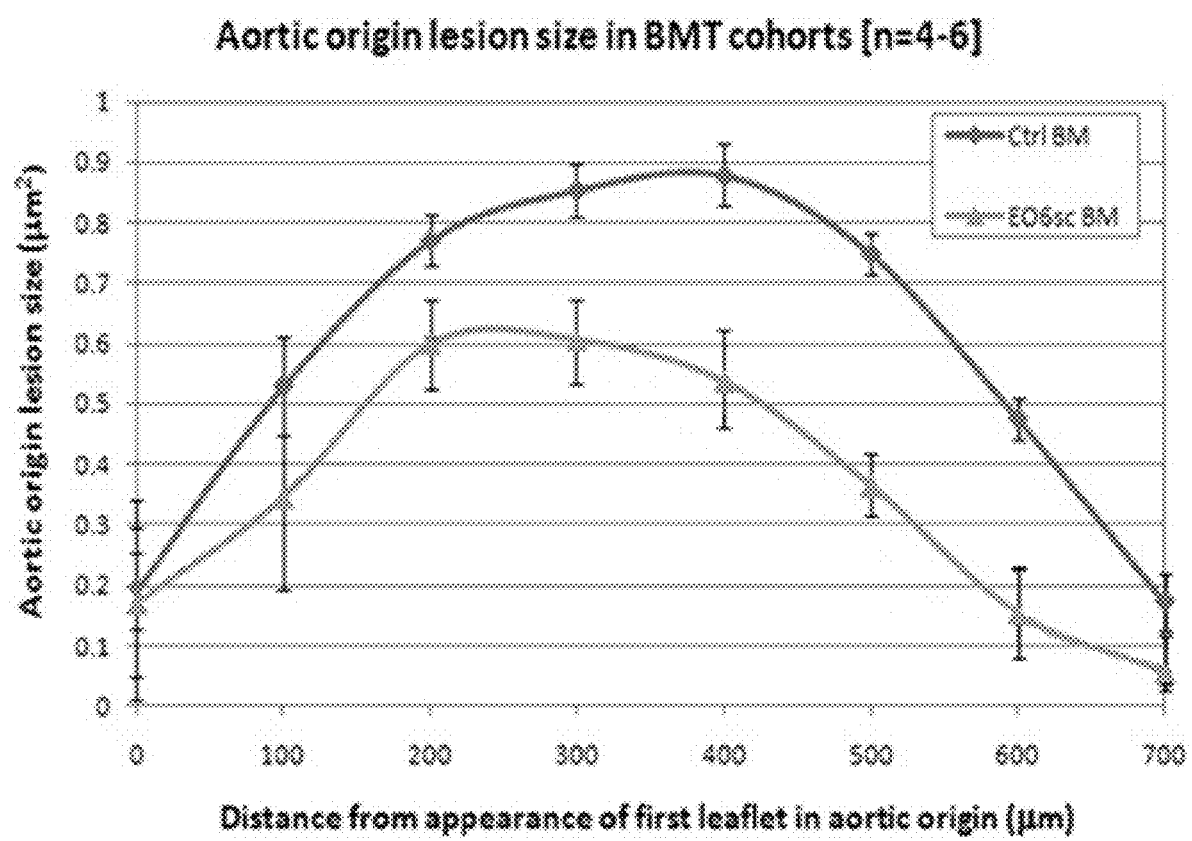
FIG. 7 provides the results of a bone marrow transplant ("BMT") of macrophages from a transgenic donor to wild type LDLR mice in comparison to control mice which received normal bone marrow. As shown, when the mice were fed cholesterol, the mice that received the transgenic bone marrow displayed lower levels of atherosclerosis at the aortic valve area.

As macrophages also secreted E06-scFv, bone marrow transplantation ("BMT") was performed by transplanting bone marrow of E06-scFv-Tg mice into irradiated Ldlr$^{-/-}$ recipients (n=10-12). Aortic root lesions decreased 31% compared to BMT with wt mice donors, despite the plasma E06-scFv titers being only 10% of that in Tg mice (see FIG. 7). Hepatic steatosis was also dramatically decreased in Tg mice as was hepatic inflammatory gene expression.

In summary, cholesterol accumulation in peritoneal macrophages was reduced by 50% and inflammatory gene expression was reduced as well. Livers from cholesterol fed mice show marked steatosis and presence of OxPL, which was dramatically reduced by the presence of E06-scFv.

Macrophage Uptake of OxLDL Studies.

Figure 8A:
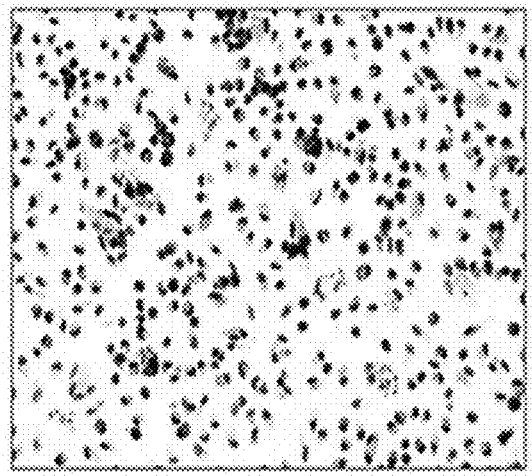
FIG. 8A-C demonstrates that E06-scFv decreased lipid uptake in elicited peritoneal macrophages of transgenic mice. (A) Oil-Red-O staining of macrophages isolated from Tg E06scFv/Ldlr$^{-/-}$ fed a high cholesterol diet for 16 weeks. (B) Ldlr$^{-/-}$ control mice fed high cholesterol diet for 16 weeks. (C) Quantification of total cholesterol accumulation in the macrophages from two groups. Peritoneal macrophages taken from the transgenic mice have ~50% less cholesterol than macrophages from wild type mice. The results are consistent with E06-scFv blocking OxLDL uptake by the macrophages leading to less cholesterol accumulation.
Figure 8B:
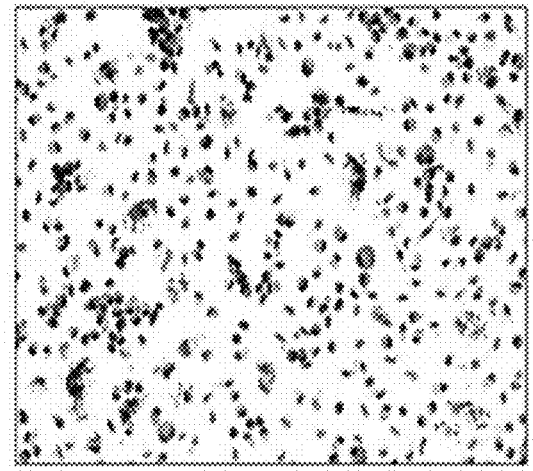
Figure 8C:
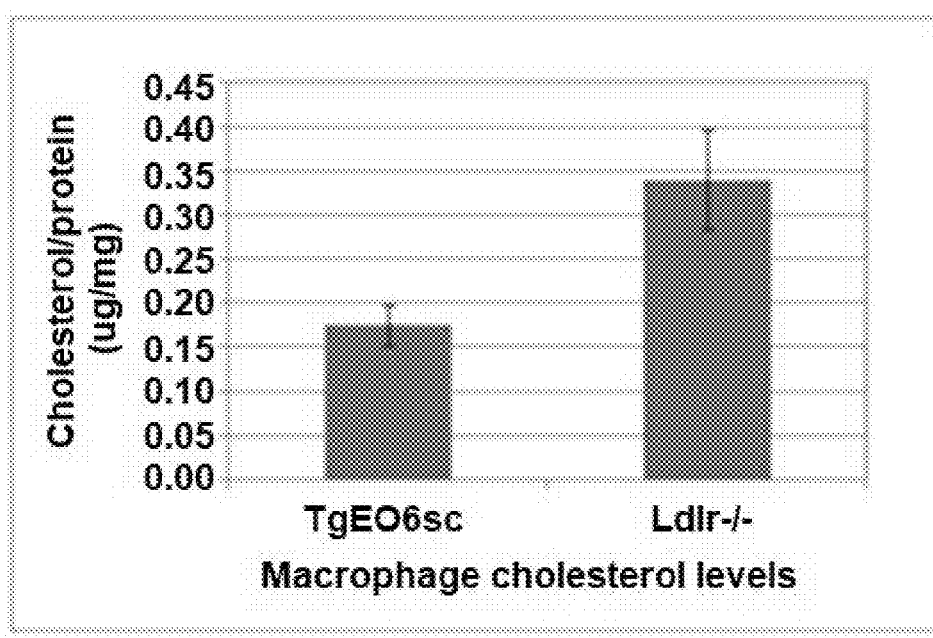
Figure 9:
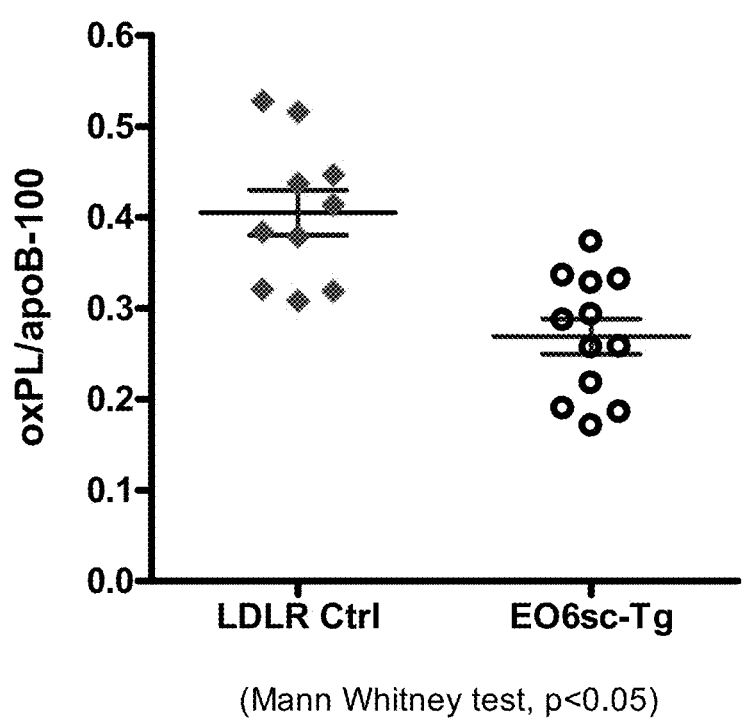
FIG. 9 provides that E06-scFv reduced the oxPL/apoB ratio in the plasma of transgenic mice fed high cholesterol diets. The plasma oxPLs (E06 epitope) on apoB-100-containing particles were measured by sandwich chemiluminescence immunoassay. Data are expressed as the RLU ratio of E06/LF3. To measure ratio of oxPL epitopes on murine apoB-100 containing particles, parallel plates were coated with LF5 to capture apoB-100, whereas biotinylated LF3 and E06 were used to detect the captured apoB and oxPL epitopes, respectively. The E06 RLUs were then divided by the LF3 RLUs to determine the oxPL/apoB ratio. OxPLs in Ldlr$^{-/-}$ control mice were significantly higher than E06-scFv transgenic mice.
Figure 10:
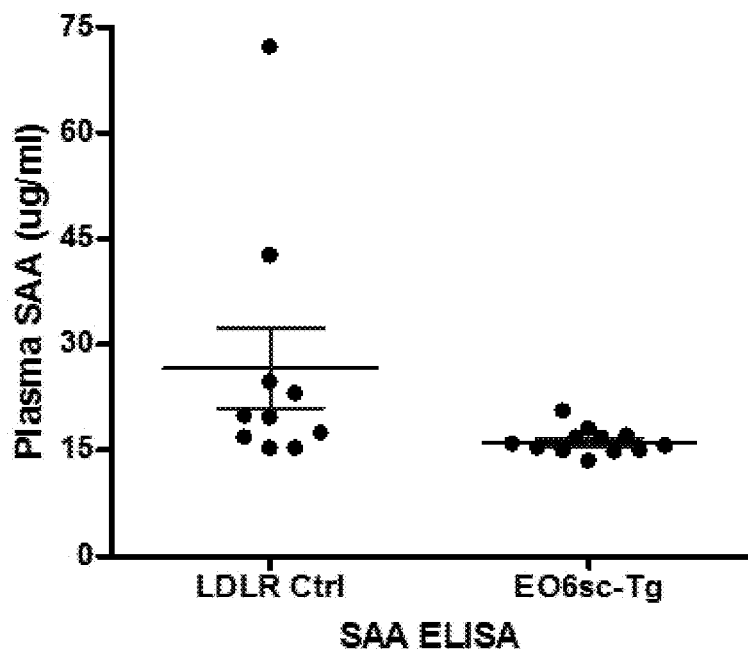
FIG. 10 provides the results of mouse serum amyloid A (SAA1) assays. SAA is an acute phase serum protein marker that is elevated in mice approximately 50-fold following LPS injection. Serum amyloid A (SAA1 and SAA2) are a family of apolipoproteins secreted as a 103aa (12 kDa) polypeptide and circulated as part of the HDL complex. SAA enhances the binding of HDL's to macrophages and helps the delivery of lipid to sites of injury for use in tissue repair.
Figure 11:
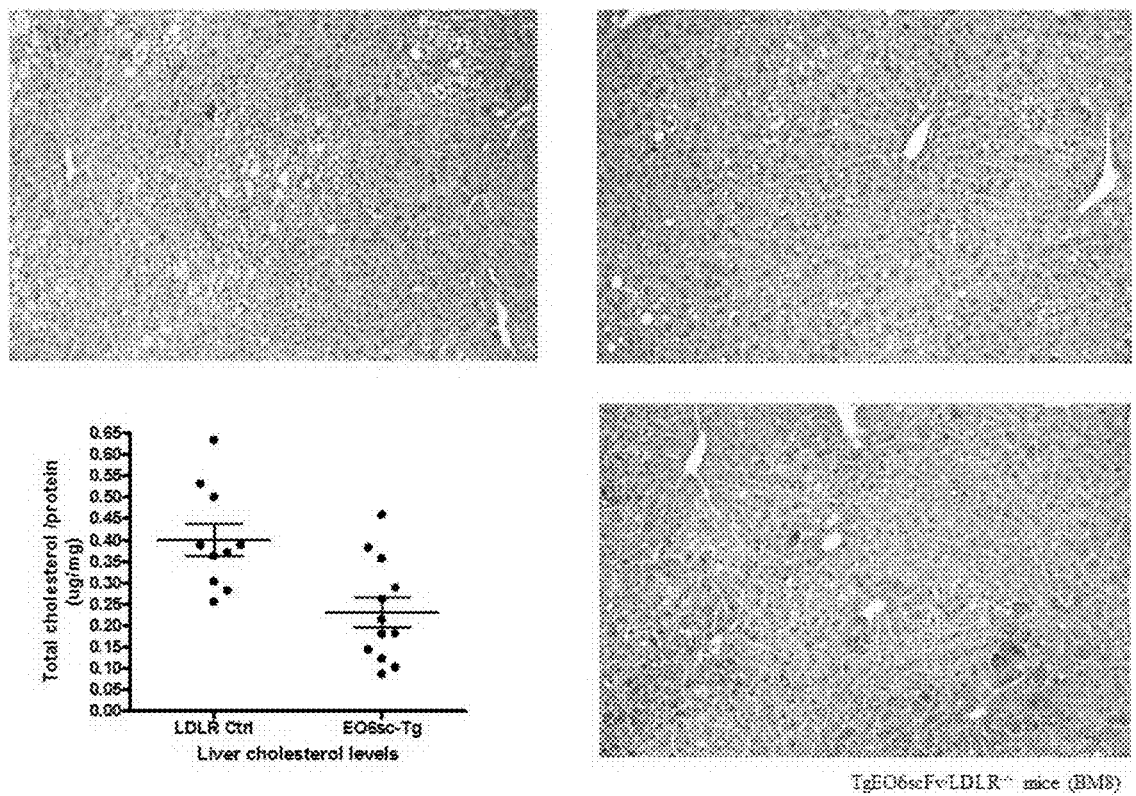
FIG. 11 demonstrates the effects of E06-scFv on lipid levels and inflammation. Hepatic paraffin slides were immunostained with F4/80 (Clone: BM8, Rat IgG2a, κ) against macrophages (Kupffer cells) in livers from Tg E06-scFv and Ldlr$^{-/-}$ mice fed high chol diet for 16-wks. Arrows point at foamy appearance of Kupffer cells clusters.
Figure 12:
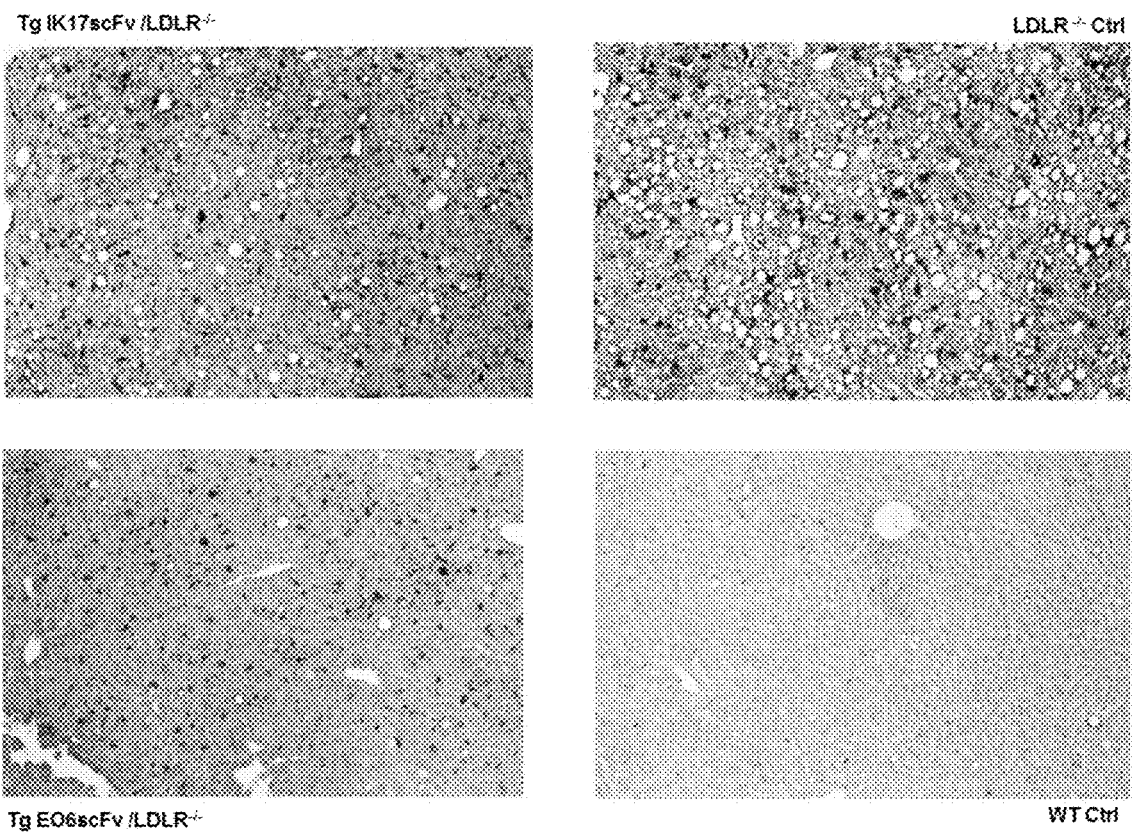
FIG. 12 provides images of Liver sections of scFv-Tg mice fed 1% cholesterol diet for 16 weeks were stained for oxPL by biotinylated E06 antibody, and visualized by ABC-HRP VectaStain kit.
Figure 13:
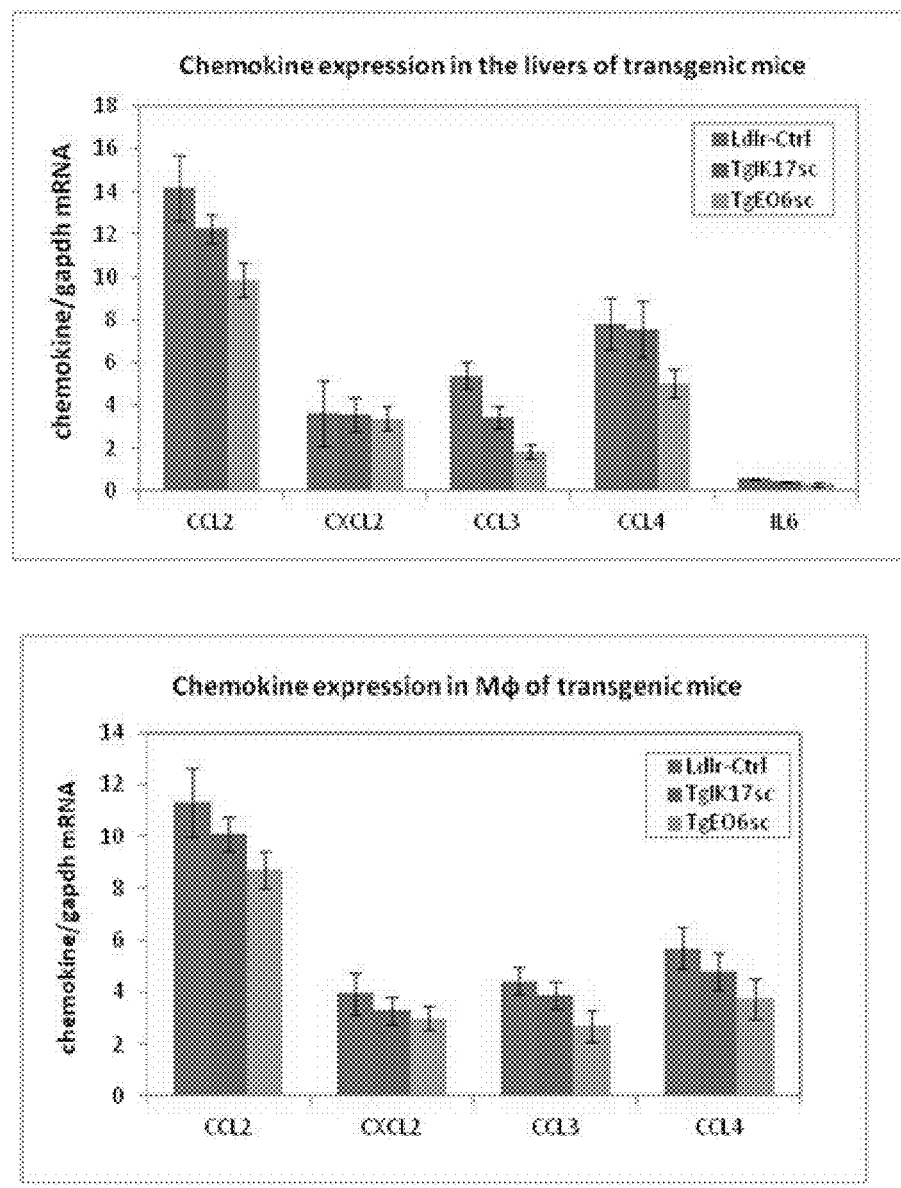
FIG. 13 demonstrates that E06-scFv reduced expression of pro-inflammatory mediators in macrophages and liver cells. Q-PCR analysis of inflammatory marker genes in livers and macrophages from transgenic mice. The mRNA levels were normalized to gapdh mRNA and expressed as means±SEM relative to the levels in controls.
Figure 14:
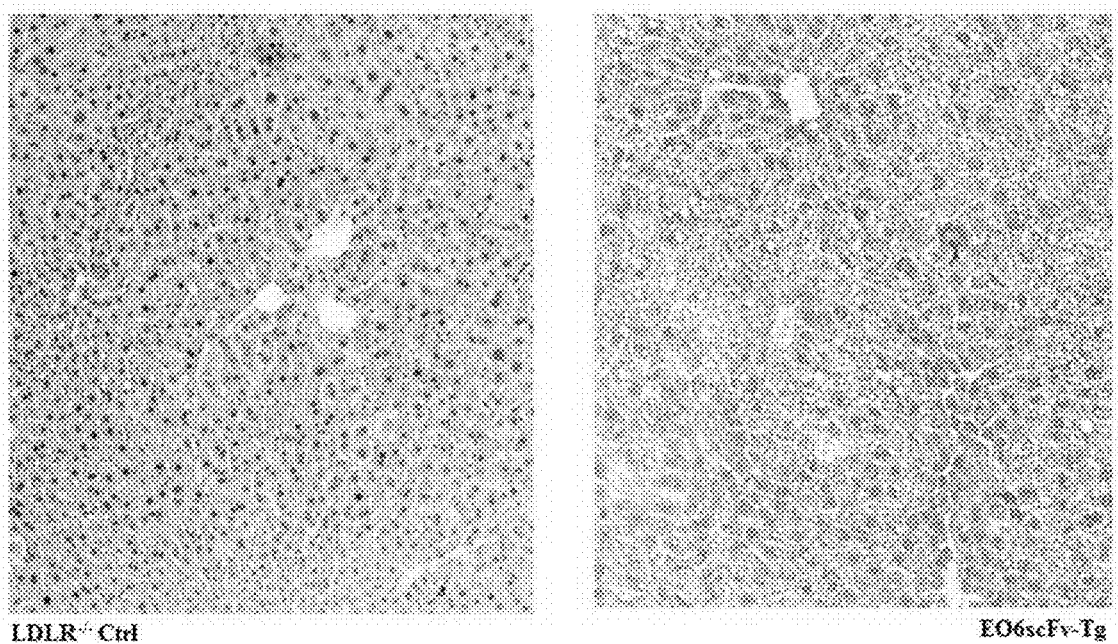
FIG. 14 provides images of liver tissues stained for the expression of single-chain E06antibody from Tg E06-scFv mice and Ldlr$^{-/-}$ control using biotinylated anti-myc tag mAb and ABC-HRP VectaStain kit.
Figure 15:
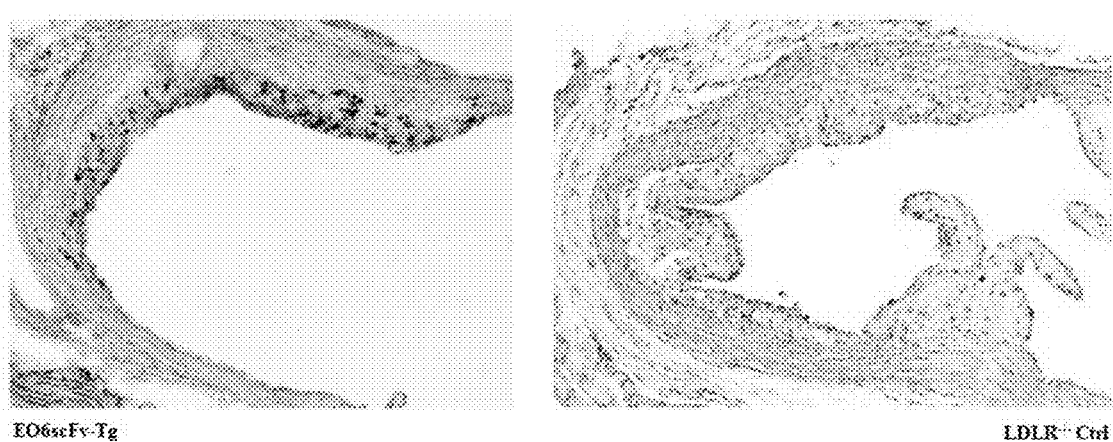
FIG. 15 shows the expression of E06-scFv in aortic lesion of Tg mice and formation of immune complex. Cross sections at the aortic valve were stained with anti-myc tag mAb to show E06-scFv immune complex in the lesions.
Figure 17:
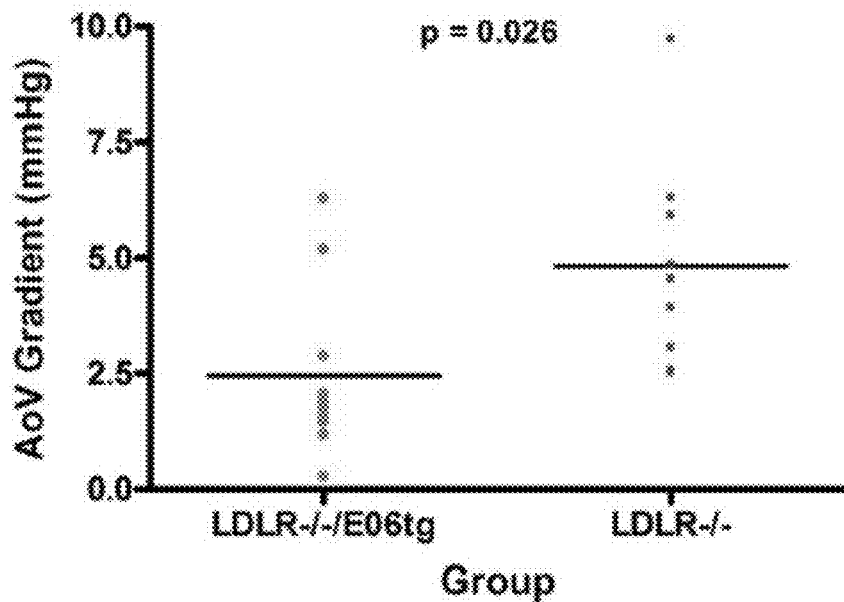
FIG. 17 shows that aortic valve gradients are lower in LDLR$^{-/-}$/E06 transgenic mice compared to LDLR$^{-/-}$ controls, consistent with the beneficial effects on valve opening.
Figure 18:
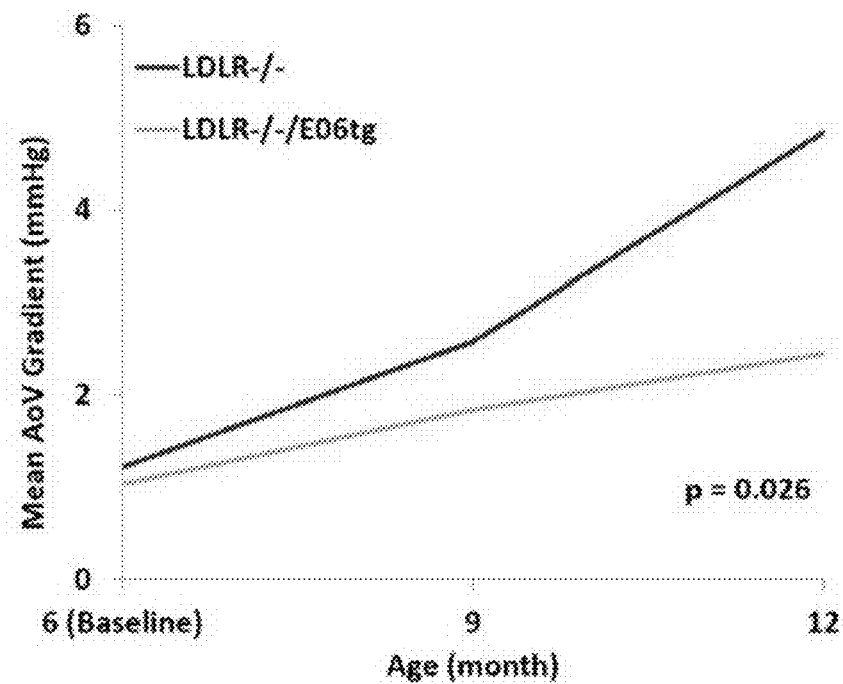
FIG. 18 shows that aortic valve gradients are lower in LDLR$^{-/-}$/E06 transgenic mice compared to LDLR$^{-/-}$ controls, consistent with the beneficial effects on valve opening.
Figure 19:
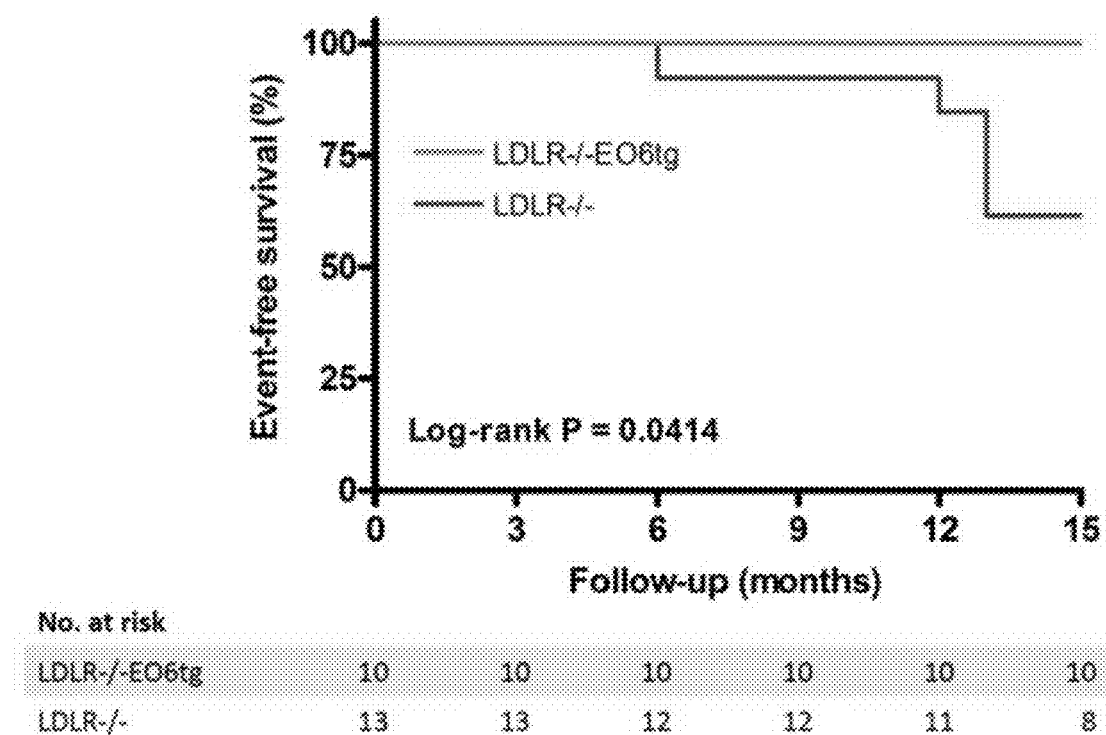
FIG. 19 shows that LDLR$^{-/-}$/E06 transgenic mice live longer compared to LDLR$^{-/-}$ controls.

E06-scFv lacks the functional effects of intact antibodies other than the ability to bind OxPL and inhibit OxLDL uptake in macrophages. Thus, these data demonstrates that OxPL are profoundly proinflammatory and proatherogenic, which can be counteracted by administering E06-scFv in vivo (see FIG. 8). Taken together, these studies suggest that E06-scFv has great potential as an anti-inflammatory agent and/or anti-atherosclerotic agent in preventing the progression of atherosclerosis and/or inflammation.

A number of embodiments have been described herein. Nevertheless, it will be understood that various modifications may be made without departing from the spirit and scope of this disclosure. Accordingly, other embodiments are within the scope of the following claims.

What is claimed is:

1. A method of treating ischemic myocardium in a subject in need thereof, the method comprising administering to the subject an antibody or a fragment thereof that specifically binds to a phosphocholine (PC) headgroup of an oxidized phospholipid, the antibody comprising: a VH comprising the complementarity determining regions (CDRs) of the VH amino acid sequence set forth in SEQ ID NO: 2; and a VL comprising the CDRs of the VL amino acid sequence set forth in SEQ ID NO: 2.

2. The method of claim 1, wherein the VH comprises the CDR amino acid sequences set forth in SEQ ID NOs: 6, 7, and 8.

3. The method of claim 1, wherein the VL comprises the CDR amino acid sequences set forth in SEQ ID NOs: 9, 10, and 11.

4. The method of claim 1, wherein the VH comprises the CDR amino acid sequences set forth in SEQ ID NOs: 6, 7, and 8, and the VL comprises the CDR amino acid sequences set forth in SEQ ID NOs: 9, 10, and 11.

5. The method of claim 1, wherein the VH comprises the VH amino acid sequence set forth in SEQ ID NO: 2.

6. The method of claim 1, wherein the VL comprises the VL amino acid sequence set forth in SEQ ID NO: 2.

7. The method of claim 1, wherein the VH comprises the VH amino acid sequence set forth in SEQ ID NO: 2, and the VL comprises the VL amino acid sequence set forth in SEQ ID NO: 2.

8. The method of claim 1, wherein the antibody or fragment comprises the amino acid sequence of SEQ ID NO: 2.

9. The method of claim 1, wherein the antibody or fragment is a chimeric antibody or humanized antibody.

10. The method of claim 1, wherein the antibody or fragment further comprises an Fc region.

11. The method of claim 10, wherein the Fc region is from an IgG, IgM, IgA, IgD, IgE antibody, or any subclass thereof.

12. The method of claim 10, wherein the Fc region is from an IgG antibody.

13. The method of claim 10, wherein the Fc region is a native Fc region.

14. The method of claim 10, wherein the Fc region is a variant Fc region.

15. The method of claim 10, wherein the antibody or fragment comprises the amino acid sequence of SEQ ID NO: 14.

* * * * *